(12) United States Patent
Krulevitch et al.

(10) Patent No.: US 11,037,465 B2
(45) Date of Patent: Jun. 15, 2021

(54) DEVICES AND METHODS FOR DRUG ADMINISTRATION AND MIXING, AND TRAINING OF PROPER TECHNIQUES THEREFOR

(71) Applicant: Janssen Pharmaceutica N.V., Beerse (BE)

(72) Inventors: Peter A. Krulevitch, Pleasanton, CA (US); Ian Scrimgeour, Dunbar (GB); Scott Martin, Edinburgh (GB); James McLusky, Edinburgh (GB); James Glencross, Edinburgh (GB); Blair Hutton, Edinburgh (GB); Nick Foley, Edinburgh (GB); Jose Antonio Buron Vidal, Parede (PT)

(73) Assignee: Janssen Pharmaceutica NV, Beerse (BE)

( * ) Notice: Subject to any disclaimer, the term of this patent is extended or adjusted under 35 U.S.C. 154(b) by 504 days.

(21) Appl. No.: 15/736,328

(22) PCT Filed: Jun. 22, 2015

(86) PCT No.: PCT/US2015/036969
§ 371 (c)(1),
(2) Date: Dec. 14, 2017

(87) PCT Pub. No.: WO2016/204795
PCT Pub. Date: Dec. 22, 2016

(65) Prior Publication Data
US 2018/0182263 A1 Jun. 28, 2018

Related U.S. Application Data

(60) Provisional application No. 62/182,426, filed on Jun. 19, 2015.

(51) Int. Cl.
*G09B 23/28* (2006.01)
*A61J 1/20* (2006.01)
(Continued)

(52) U.S. Cl.
CPC ............. *G09B 23/28* (2013.01); *A61J 1/16* (2013.01); *A61J 1/2055* (2015.05); *A61J 1/2096* (2013.01);
(Continued)

(58) Field of Classification Search
CPC ....... G09B 23/28; G09B 23/285; A61J 1/2055
See application file for complete search history.

(56) References Cited

U.S. PATENT DOCUMENTS 6,039,557 A 3/2000 Unger et al.
6,332,704 B1 12/2001 Gasser et al.
(Continued)

FOREIGN PATENT DOCUMENTS

CN 101218611 7/2008
CN 102123751 7/2011
(Continued)

OTHER PUBLICATIONS

International Search Report dated Nov. 17, 2015; International Application No. PCT/US2015/036969.
(Continued)

*Primary Examiner* — Peter R Egloff
(74) *Attorney, Agent, or Firm* — Steven J. Schwarz

(57) ABSTRACT

A device for training users in a proper mixing of pharmaceutical components, or for aiding in the mixing, or for performing the mixing, and administration of pharmaceutical components is disclosed. The device comprises a housing for receiving a pharmaceutical delivery device containing the pharmaceutical components. There is also a microcontroller disposed in the housing and a motion/
(Continued)

orientation detection device disposed within or on the housing and in communication with the microcontroller. A method for use of the device is also disclosed, along with a substance for use as one of the pharmaceutical components.

24 Claims, 25 Drawing Sheets

(51) Int. Cl.
*A61J 1/16* (2006.01)
*G09B 5/02* (2006.01)
*A61J 7/00* (2006.01)
*A61M 5/178* (2006.01)

(52) U.S. Cl.
CPC .......... *A61J 7/0053* (2013.01); *A61M 5/1782* (2013.01); *G09B 5/02* (2013.01); *G09B 23/285* (2013.01); *A61J 2200/70* (2013.01); *A61M 2205/50* (2013.01); *A61M 2205/581* (2013.01)

(56) References Cited

U.S. PATENT DOCUMENTS

| | | |
|---|---|---|
| 6,626,912 B2 | 9/2003 | Speitling |
| 7,591,801 B2 | 9/2009 | Brauker et al. |
| 8,032,251 B2 | 10/2011 | Monn |
| 8,118,776 B2 | 2/2012 | Lampropoulos et al. |
| 8,556,867 B2 | 10/2013 | Krulevitch et al. |
| 8,674,656 B2 | 3/2014 | Iio et al. |
| 8,784,381 B2 | 7/2014 | Watanabe et al. |
| 8,807,131 B1 | 8/2014 | Tunnell et al. |
| 9,022,988 B1 | 5/2015 | Shaban |
| 2005/0174430 A1* | 8/2005 | Anderson .......... H04N 1/00164 348/207.1 |
| 2008/0059133 A1 | 3/2008 | Edwards et al. |
| 2010/0094455 A1 | 4/2010 | Dehlin et al. |
| 2011/0253139 A1 | 10/2011 | Guthrie et al. |
| 2012/0295240 A1 | 11/2012 | Walker et al. |
| 2014/0193788 A1 | 7/2014 | Groves et al. |
| 2014/0322682 A1 | 10/2014 | Baym et al. |
| 2014/0350525 A1 | 11/2014 | Robinson et al. |
| 2015/0051538 A1 | 2/2015 | Hata et al. |
| 2018/0304018 A1* | 10/2018 | Blondino .......... A61M 5/28 |

FOREIGN PATENT DOCUMENTS

| | | |
|---|---|---|
| CN | 102245257 | 11/2011 |
| CN | 102300597 | 12/2011 |
| CN | 102413759 | 4/2012 |
| CN | 102614565 | 8/2012 |
| CN | 102099071 | 8/2013 |
| CN | 102202703 | 8/2014 |
| DE | 10057616 | 5/2002 |
| EP | 2541532 | 1/2013 |
| JP | H02-126858 | 5/1990 |
| JP | H03-139688 | 6/1991 |
| JP | 2010/178814 | 8/2010 |
| JP | 2015-100096 | 5/2015 |
| RU | 2192285 | 11/2002 |
| RU | 2192894 | 11/2002 |
| RU | 2405574 | 12/2010 |
| RU | 138718 | 3/2014 |
| SU | 1286264 | 1/1987 |
| SU | 1651316 | 5/1991 |
| WO | WO 2009/141005 | 11/2009 |
| WO | WO 2010/021953 | 2/2010 |
| WO | WO 2011/139198 | 11/2011 |
| WO | WO 2013/069305 | 5/2013 |
| WO | WO 2014/080636 | 5/2014 |
| WO | WO 2016/203058 | 12/2016 |
| WO | WO 2016/203059 | 12/2016 |
| WO | WO 2016/204795 | 12/2016 |
| WO | WO 2016/207119 | 12/2016 |

OTHER PUBLICATIONS

International Search Report dated Aug. 24, 2016; International Application No. PCT/EP2016/064227.
International Search Report dated Aug. 26, 2016; International Application No. PCT/EP2016/064228.
International Search Report dated Aug. 26, 2016; International Application No. PCT/EP2016/064229.

* cited by examiner

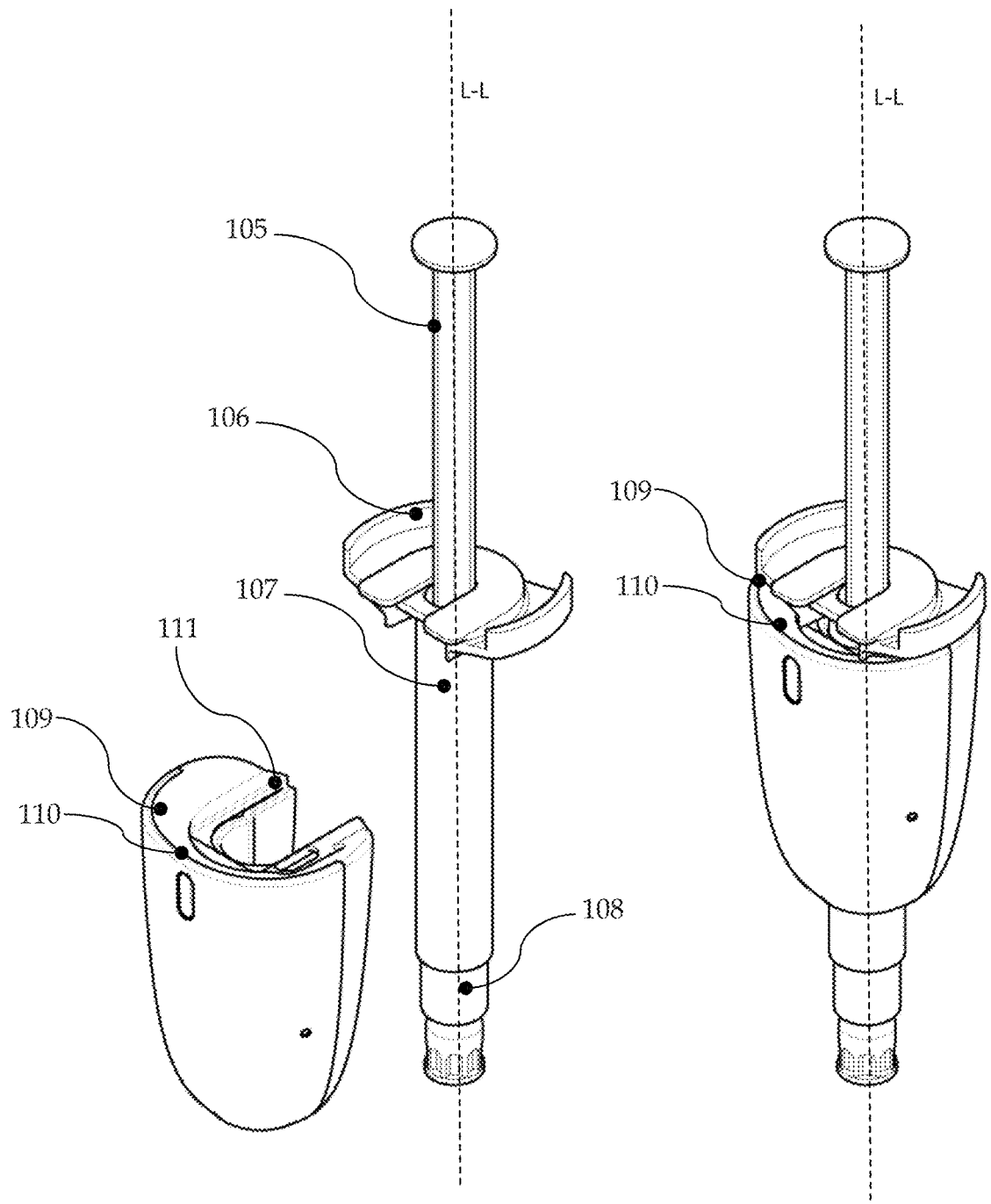

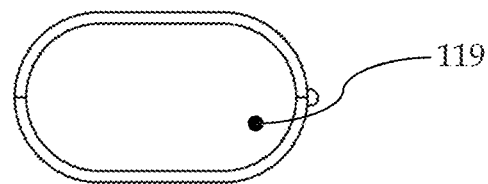
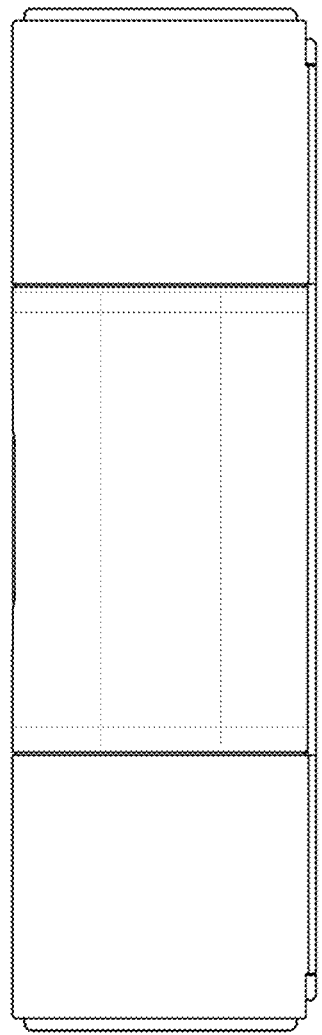
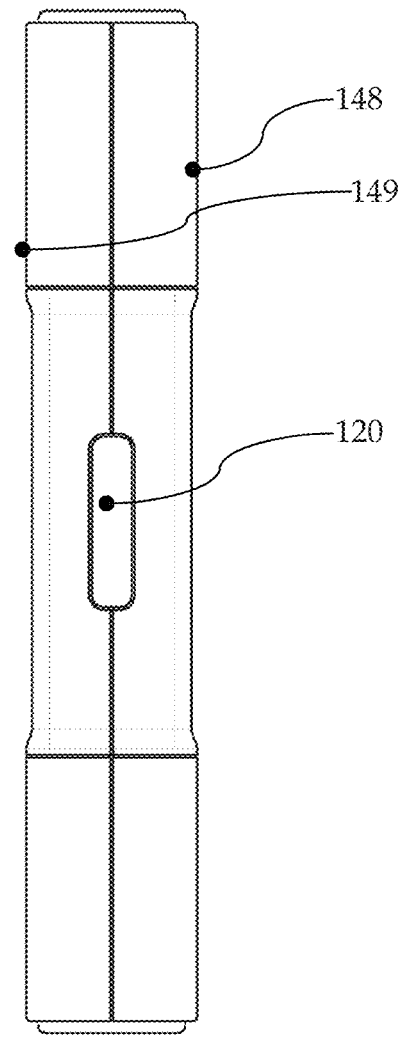

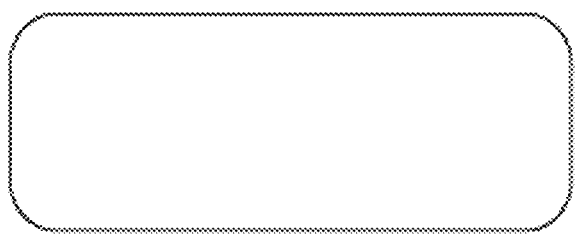
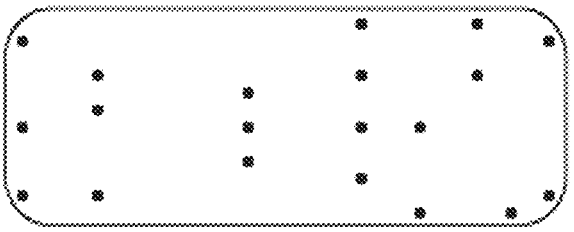
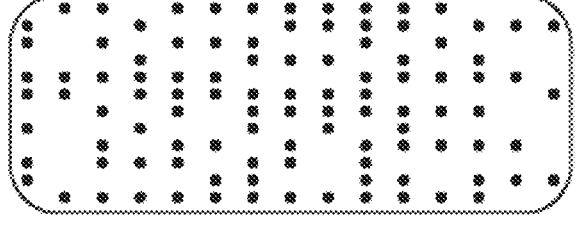
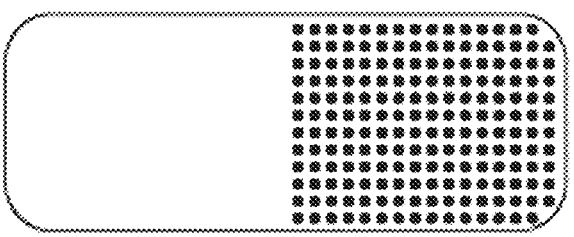

DEVICES AND METHODS FOR DRUG ADMINISTRATION AND MIXING, AND TRAINING OF PROPER TECHNIQUES THEREFOR

BACKGROUND

Pharmaceutical products intended for delivery by injection may be stored in vials or pre-filled syringes. In either case, when such products consist of two or more liquid and/or solid phases, they must be agitated prior to administration for optimum result, usually by manual shaking. Health Care Professionals (HCPs) and in some cases patients or caregivers, may not provide consistent agitation for a number of reasons. They may not be familiar with the pharmaceutical product; they may have habituated experience of similar pharmaceutical products which they presume to have the same or similar preparation steps; or they may mis-time the shake duration or required shaking vigor, mistakenly underestimating the time or vigor required to properly agitate the device and adequately mix the product.

SUMMARY OF THE DISCLOSURE

We have identified a need for a device that would provide the HCP with the knowledge and experience of the minimum duration and vigor of shaking required for the preparation of various pharmaceutical products such as, for example, INVEGA TRINZA™, which consists of particles in a suspension. We have also identified a need for a device that alerts the user when too much time has expired after mixing and the mixing step must be repeated. Yet another need that we have identified is to ensure that the device only works with the specified syringe for a particular product, and not, for example, a competitor syringe. This ensures that people do not mistakenly use the device with the wrong drug product, and can also be used as a means for differentiating one product relative to a competitor.

Accordingly, we have devised various embodiments of devices and methods to operate such devices to fulfill the needs or mitigate the shortcomings that we have identified above. In one aspect of the invention, we have devised a device for training users how to properly mix pharmaceutical components. In another aspect, we have devised a device for mixing and assisting with the administration of properly mixed pharmaceutical components. In another aspect, we have devised a device for mixing and administrating properly mixed pharmaceutical components. In another aspect, we have devised a device for attachment to a pharmaceutical delivery device and for assisting with the administration of properly mixed pharmaceutical components. All of these devices are referenced herein (in both the description and claims) as the "device". The device includes a housing that extends along a longitudinal axis with a power source disposed in the housing and a microcontroller disposed in the housing and electrically powered by the power source as well as a user notification device and an accelerometer disposed in the housing and electrically connected to the microcontroller. In this device, the microcontroller is configured to detect a motion and orientation of the housing and indicate via the user notification device as to whether the motion or orientation of the housing being shaken during one of a drug administration or a training event is sufficient with respect to predetermined thresholds including magnitude of the force applied during the shaking, the orientation of the housing and duration of such shaking.

Another aspect of the invention includes a method of operating such a device. The method can be achieved by determining from the accelerometer if the magnitude of the motion and orientation of the housing are sufficient with respect to predetermined thresholds including magnitude of the force applied during the shaking, the orientation of the housing and duration of such shaking; and announcing via the user notification device as to whether the motion or orientation of the housing being shaken during one of a drug administration or a training event meets the predetermined thresholds.

In addition to the various aspects described above, other features recited below can be utilized in conjunction therewith to arrive at different permutations of the invention. For example, the device may include a start switch electrically connected to the microcontroller; the accelerometer may include a 3-axis accelerometer; the accelerometer is configured to activate the microcontroller upon detection of movements of the housing during one of a drug administration or a training event; the microcontroller is configured to detect when shaking of the housing has ended prematurely, or if the level of shaking vigor has reduced to a level below the pre-set threshold, to enter a pause mode to allow the user to restart the shaking during one of a drug administration or a training event; the microcontroller is configured to set a timer and determine when a maximum allowable time after shaking of the housing has elapsed to warn the user to shake the device again during one of a drug administration or a training event; the housing may include a syringe barrel element with finger flange and one end and a barrel tip spaced apart along the longitudinal axis; the housing may include a body with a slot sized to accept a syringe barrel; the housing may include a housing provided with a compartment and a lid to receive an entire syringe; the housing may include an elongated body approximately the same length as a syringe barrel such that a syringe is inserted into a syringe receiving hole in the body and retained by the compressive force applied by the finger-like members between a syringe finger flange and a body base; the housing may include a body with a syringe accepting slot sized to accept a syringe barrel; the housing may include a puck-like body with a syringe accepting hole so that in use a syringe is inserted into the syringe accepting hole and is held in place with a user's thumb on an underside thumb grip.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE FIGURES

The foregoing and other features and advantages of the invention will be apparent from the following, more particular description of preferred embodiments of the invention, as illustrated in the accompanying drawings.

FIGS. 3A and 3B illustrate a syringe barrel attachment embodiment, showing device separate from, and attached to a syringe;

FIGS. 9A to 9C illustrate a syringe case embodiment, general view showing front, top and side view;

FIGS. 26A to 26D illustrate LCD screen conditions showing stages of mix from sediment on left to mix on the right;

The accompanying drawings, which are incorporated herein and constitute part of this specification, illustrate presently preferred embodiments of the invention, and, together with the general description given above and the detailed description given below, serve to explain features of the invention (wherein like numerals represent like elements).

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Figure 1A:
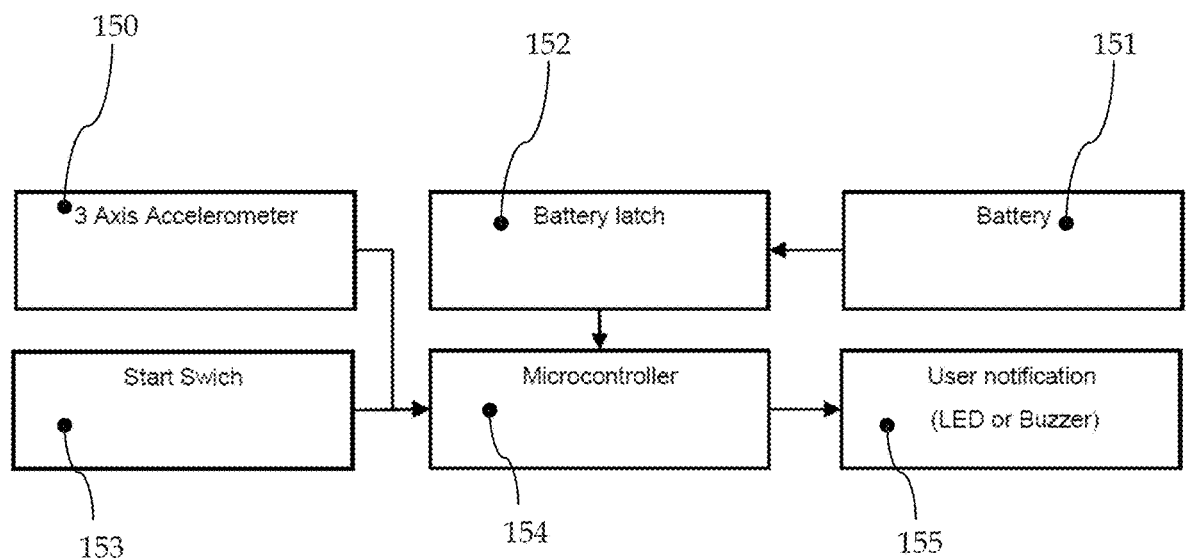
FIG. 1A is a block diagram schematic of the electronic system.

The exemplary embodiments shown and described here may utilize an electronic system such as an electronic circuit mounted on a printed circuit board (PCB), which may include means to supply and control electrical power, means to measure spatial acceleration, means to time the duration of shaking and means to communicate the device state to the user as shown in FIG. 1A.

FIG. 1A illustrates a schematic overview of the electronic system that can be utilized with various embodiments described and illustrated herein. It is noted that for these embodiments, the forces are measured preferably using a 3-axis accelerometer 150 because the user's shaking movement will likely be in more than one direction and furthermore sufficient acceleration may be a factor of accelerations in multiple directions. Hence, a threshold may be determined to be a function of one or more acceleration directions. Additionally the system may include a start switch 153, which may be a manually activated switch, or preferably may be an acceleration activated switch to wake up the circuit, thus conserving battery power when the device is not in use. The advantage of the acceleration activated switch is that the user need only start shaking the device to switch it on. In some embodiments it may be preferable to require the user to make a conscious decision to switch the device on, and carry out a specific explicit action to switch the device on, hence the manual switch may be preferable. Once the device has woken up, the battery latch 152 ensures power is supplied from the battery 151 for sufficient time to complete the shake cycle and provide feedback to the user.

A further development of this embodiment is described as follows. Time is measured using a microcontroller 154, microprocessor or timer; from the moment that shaking is first detected. The electronic system is programmed with an algorithm which compares the measured shake acceleration and duration with a preset threshold. The electronic system compares the recorded elapsed time and force measurements and returns a communication signal corresponding to the device state 155. The device state is communicated using one or preferably a combination of the following: visual feedback such as light emitting diode (LED), graphical display such as Liquid Crystal Display (LCD); audible feedback such as an audible buzzer or polyphonic speaker; tactile feedback such as vibration motor. Such an electronic circuit requires a power source, such as a battery, that may be rechargeable or not. If not rechargeable, the battery may be replaceable or it may not be replaceable, in which case the device must be disposed of in its entirety at end of life, defined by the end of the battery life.

The electronic circuit is contained inside the device, with visual feedback means visible to the user by way of a window or light transmitting element. The electronic circuit affords additional design features:

Pause Function.

The program may allow the system to detect when shaking has ended prematurely, or if the level of shaking vigor has reduced to a level below the pre-set threshold, using the accelerometer or acceleration activated switch. If such events are detected the device may enter a pause mode, which pauses the timing process and may indicate to the user that the device has entered pause mode. The indication to the user may be a pause in the feedback being provided, such as a pause in the audible tone, or a pause in the tactile vibration; or it may be by other means such as a state change on a light or screen. The user, upon receiving the pause indication may then correct their actions, by recommencing the shake action or increasing the vigor of the shake action, at which moment the device switches out of pause mode and recommences with the timing and force monitoring process, starting from the time count at which it paused. If the device is in pause mode for a significant amount of time such that the particles may have started to re-form a sediment, the timer will be reset.

Syringe Administration Timer.

A timer may be used to warn the user that too much time has elapsed since the device was shaken. After shaking, the particles will slowly return to a sediment state; therefore there is a maximum time limit between shaking the device and administering the injection. In some scenarios, the user may shake the device correctly, but then may be distracted long enough for the particles in the syringe to resediment. A timer may be set such that when the max allowable time after shaking of the housing has elapsed, the user is warned to shake the device again before administration. This warning could be communicated using several methods. As examples, an audible buzzer could sound when the maximum time has elapsed, or a green light which was illuminated to indicate shaking has completed could switch off.

Low Battery Warning.

Such an electronic system requires a power source, preferably a battery cell. When the remaining power in the battery has reduced to a point where device functionality may soon become impaired, the device may indicate to the user that a battery failure is imminent, and that the battery must be replaced. The device could shut down in such an event so that it may not be used until the battery has been replaced. This would prevent a potential device malfunction.

Error Warning.

Such an electronic system can perform self-checks on the system and main components so that when errors are detected the user may be given warning. It can perform such self-checks whenever the device is awoken for a shake cycle and immediately communicate that it has entered an error mode. This prevents the user from using a faulty device and prompts them to take remedial action, for example to return the device to the manufacturer, and use a replacement device.

Information Distinguishing Force and Time.

In the first instance this invention is described as providing the user with information on the success of the shake action as a single piece of information, when both sufficient time AND sufficient vigor have been achieved. An alternative arrangement of such an electronics system can provide feedback to the user on the constituent elements; in that two pieces of information are provided, the elapsed time and the level of vigor over that time. That way if a user fails to achieve the combination of sufficient time and vigor they may consult the information provided and determine the reason they were unable to be successful, they may determine if they failed to shake for sufficient time, or if they failed to shake with sufficient vigor.

Drug Expiration Alert.

A development of such an electronic system incorporates means to read the expiration data on the syringe and warn the user if it has expired. If the user were informed that the expiration date had expired they could dispose of the expired syringe and use another that had not expired. Such a system uses scanning components that read a barcode or text on the syringe to gather the expiration date, or may communicate with a chip on the syringe that contains the lot and expiration information, and compares the date to an internal clock and calendar programmed into the processor and gives an alert if the gathered date is before that on the internal clock and calendar.

The features described and illustrated above can be embodied in the following Embodiments 1-8 with highlights in the variations and differences between each embodiment described with reference to the drawing figures indicated below.

Embodiment 1. Mimic

Figure 1B:
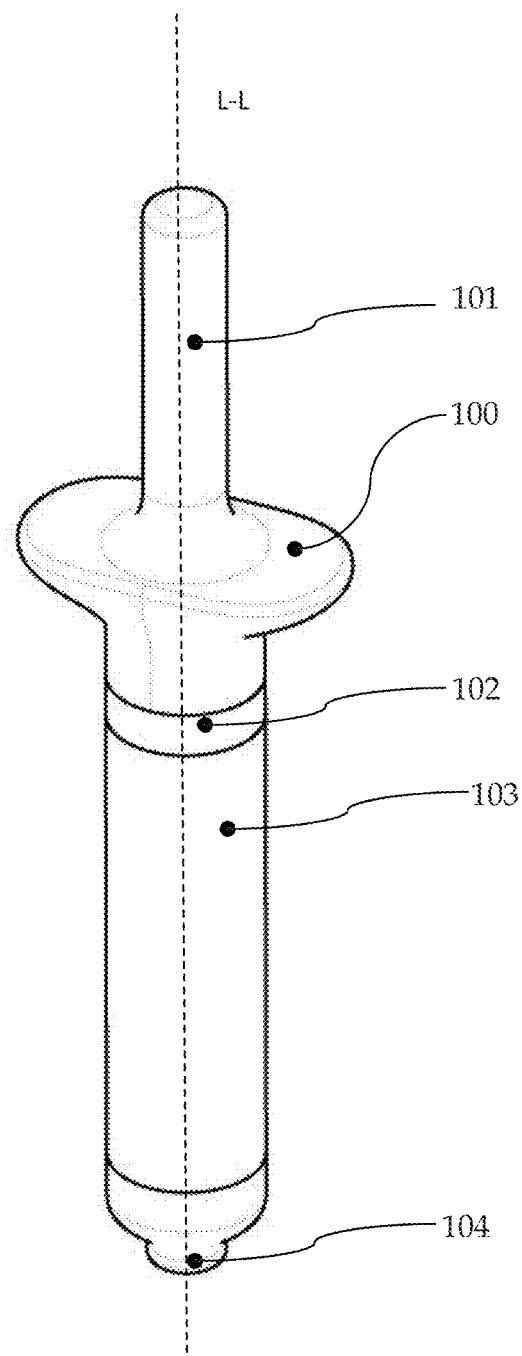
FIG. 1B illustrates a standalone mimic trainer embodiment, general view.
Figure 2A:
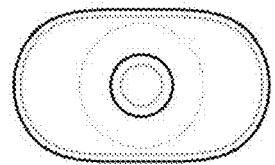
FIGS. 2A to 2D illustrate orthographic views of a standalone mimic trainer embodiment.
Figure 2B:
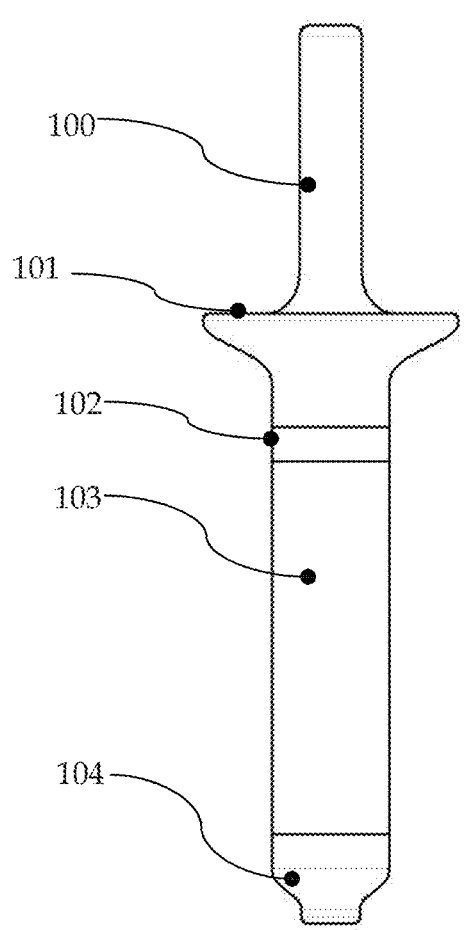
Figure 2C:
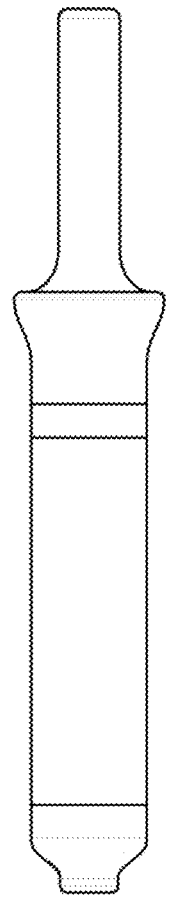
Figure 2D:
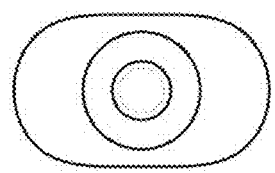

The trainer embodiment (FIG. 1B and FIGS. 2A to 2B) uses a form factor for a housing that mimics that of a syringe. It may include a syringe barrel element 103, with finger flange 100 at one end and a barrel tip 104 at the other. The distance between finger flange 100 and barrel tip 104 are similar to that of a syringe such that it may be held in a similar fashion. At the top of the form is a cylindrical portion 100 that represents a syringe plunger rod. The barrel 103 includes a light emitting feedback window 102, through which light is emitted to communicate the state of the device. In the preferred embodiment, amber light is used to indicate the device is running through a shake cycle and is monitoring the level of agitation imparted on it; green light is used to indicate the shake cycle is complete and sufficient shaking has occurred. When not in use, the light is off to conserve battery power and also to indicate that the shake cycle has not yet commenced.

Embodiment 2—Attach

Figure 4A:
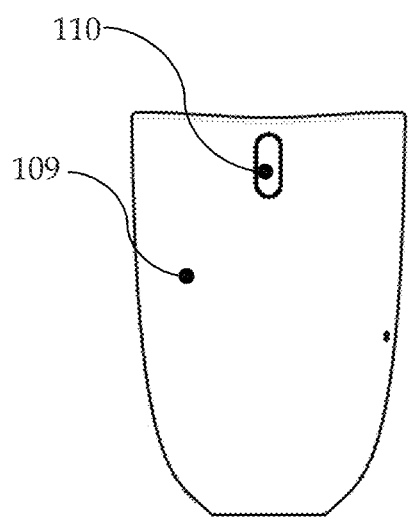
FIGS. 4A and 4C illustrates a syringe barrel attachment embodiment, front, left and right side.
Figure 4B:
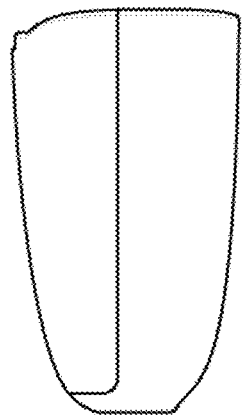
Figure 4C:
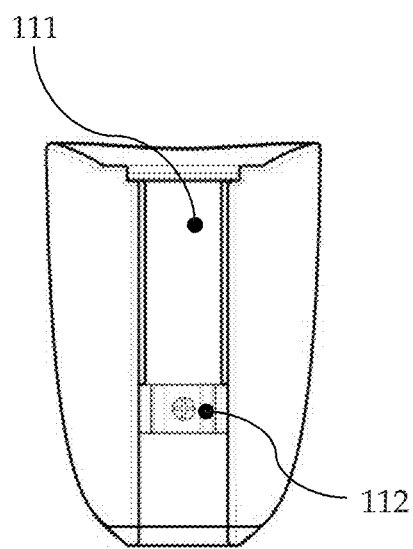
Figure 5A:
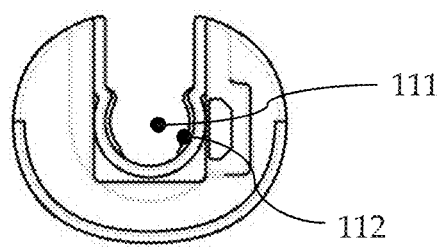
FIGS. 5A to 5C illustrate a syringe barrel attachment embodiment, front, top and bottom side.
Figure 5B:
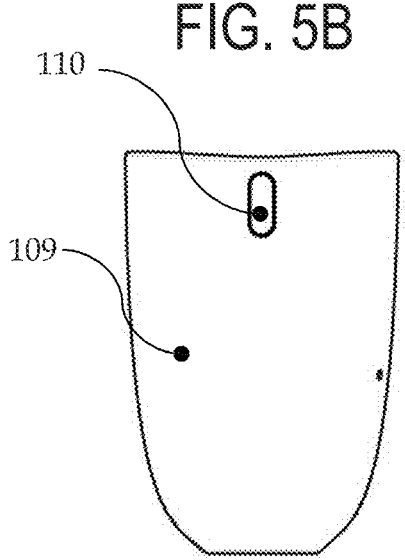
Figure 5C:
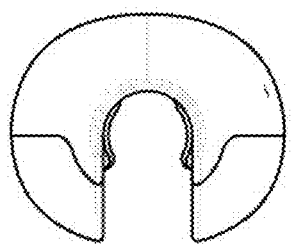
Figure 6:
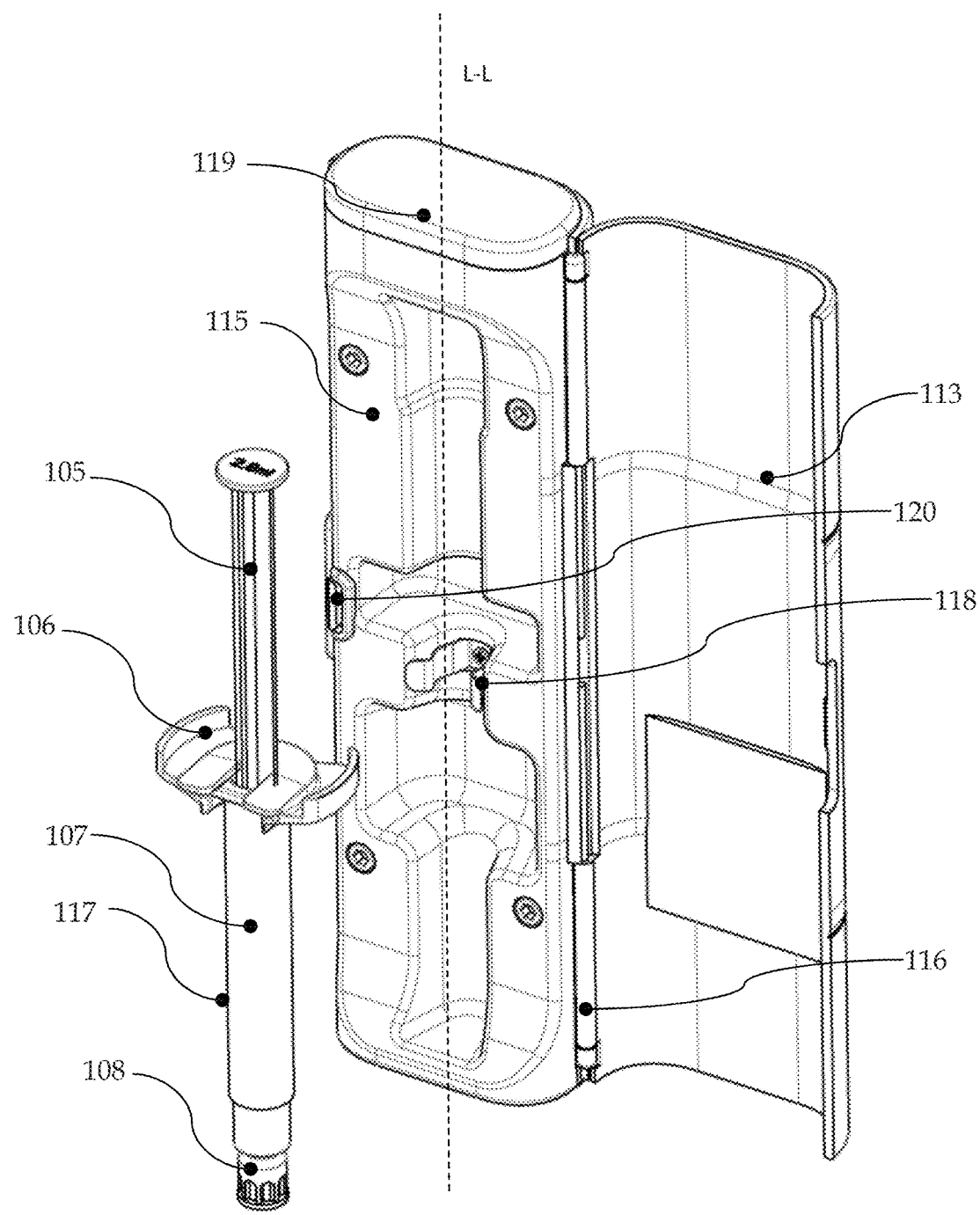
FIG. 6 illustrates a syringe case embodiment, general view showing syringe next to open case.

The embodiment shown in FIG. 3-FIG. 5 attaches to the syringe and provides feedback to the user while they are shaking the syringe. The device housing may include a body 109 with a slot 111 sized to accept a syringe barrel 107. A clip 112 (FIGS. 4A to 4C) in the slot 111 retains the syringe. Once the device housing is attached to a syringe, the shaking motion is measured using the internal electronic system, and the device state is communicated in two simultaneous ways. The first communication method is with light emitted from the light emitting feedback window 110. An amber light indicates that a shake cycle is in progress, and a green light indicates that it is completed. The second simultaneous feedback method is audible. An intermittent audible buzzing tone indicates that the shake cycle is in progress, which changes to a continuous tone when the shake cycle is completed. Furthermore, the intermittent tone emitted during the shake cycle is set at a frequency of approximately 3 Hz to reinforce the frequency and speed of shake required for optimum mixing, exploiting the tendency for humans to match repetitive behavior to percussive audible tones.

Embodiment 3—Case

Figure 7:
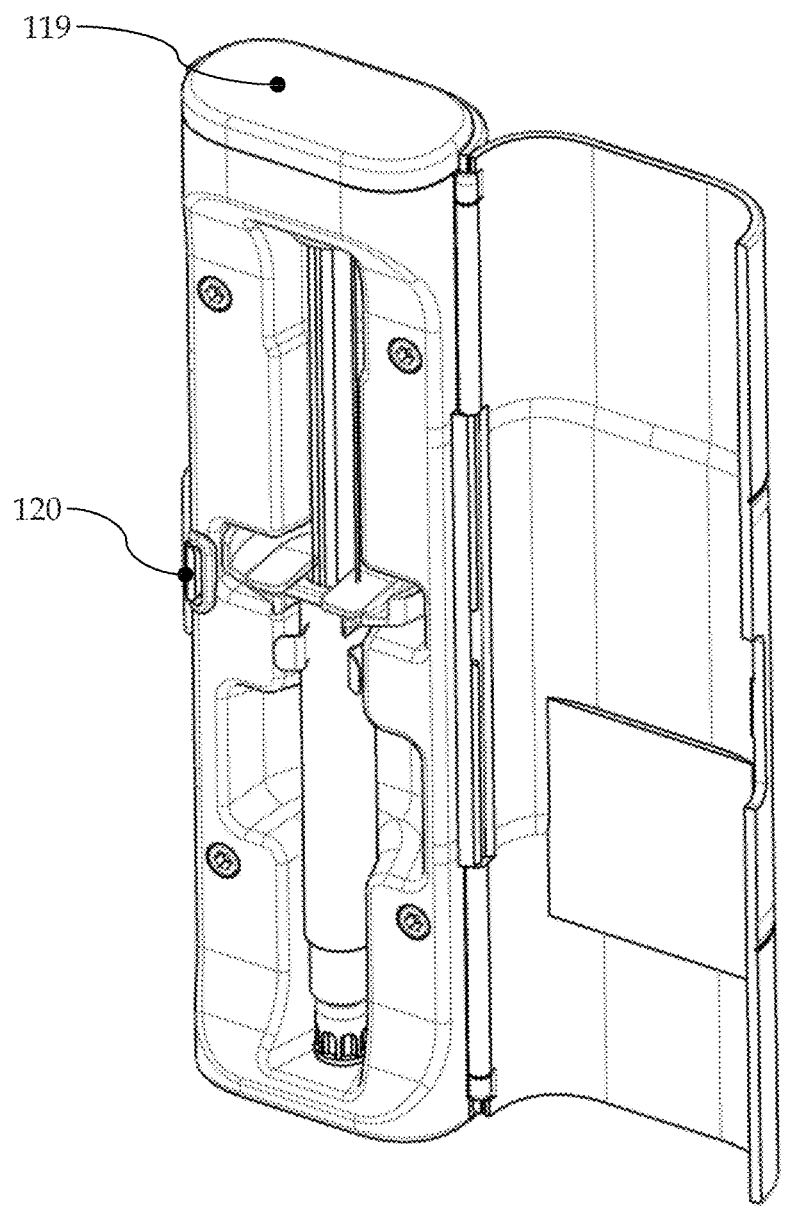
FIG. 7 illustrates a syringe case embodiment, general view showing syringe inside open case.
Figure 8:
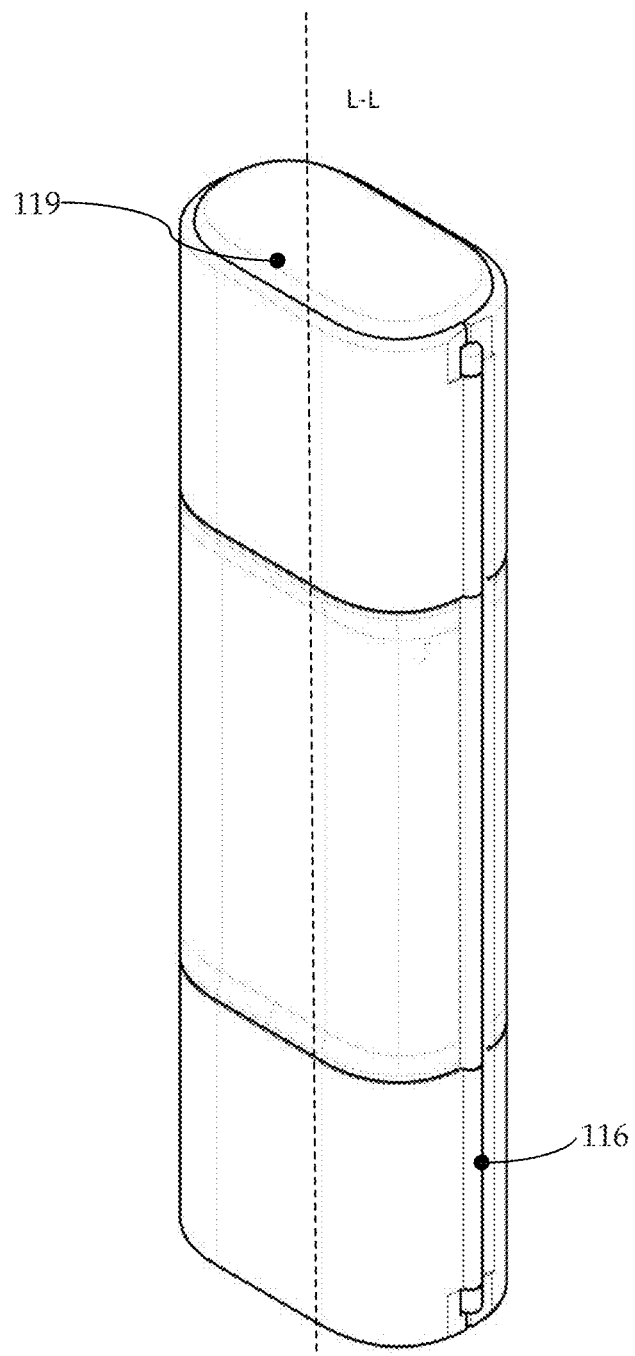
FIG. 8 illustrates a syringe case embodiment, general view showing closed case.
Figure 10A:
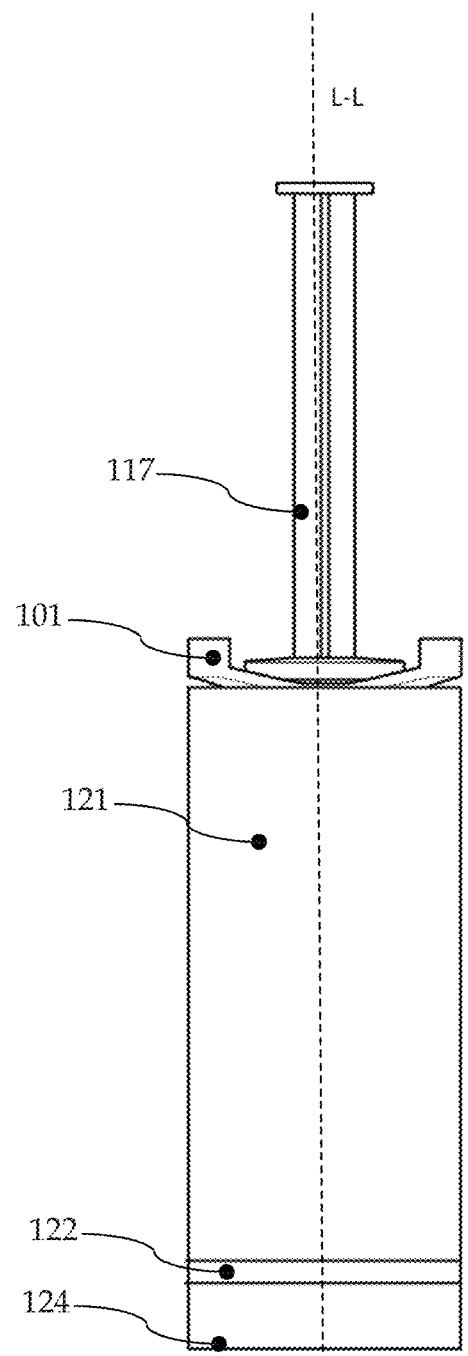
FIGS. 10A and 10B illustrate a syringe pot embodiment with syringe inside, showing front and side views.
Figure 10B:
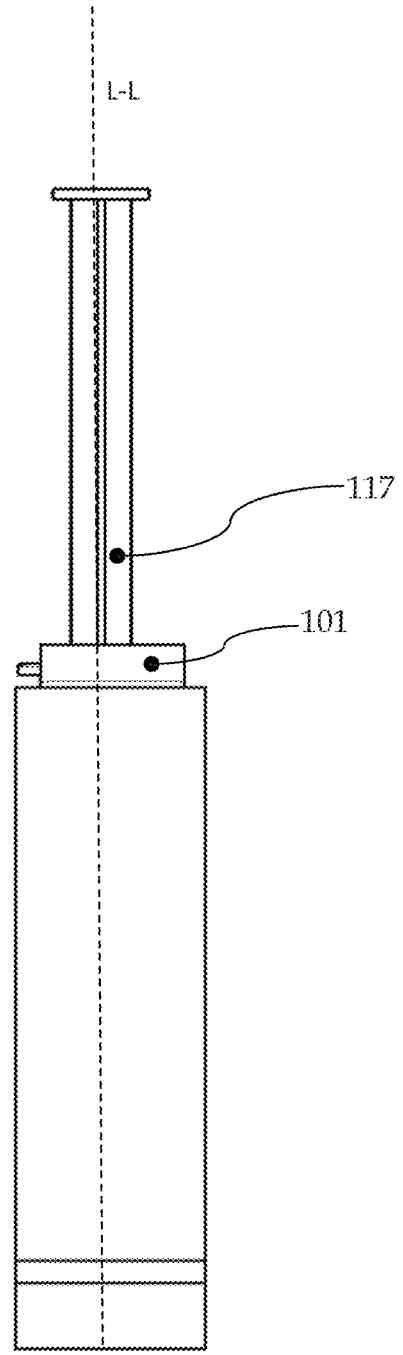
Figure 11A:
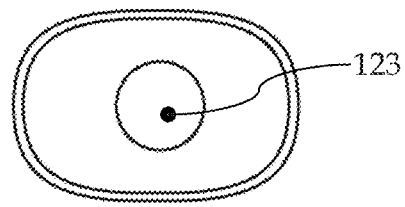
FIGS. 11A to 11C illustrate a syringe pot embodiment without syringe showing front and side views.
Figure 11B:
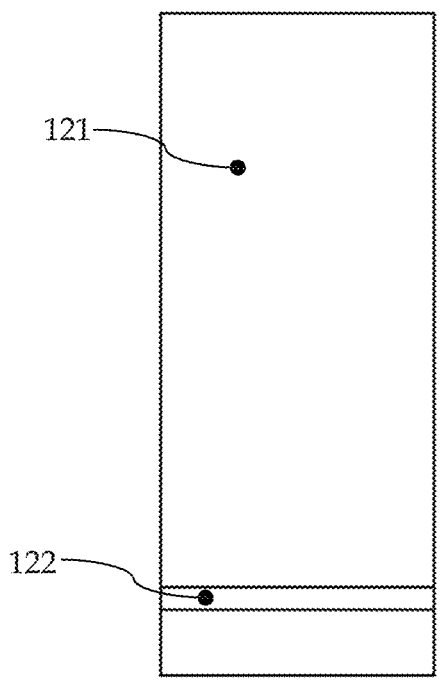
Figure 11C:
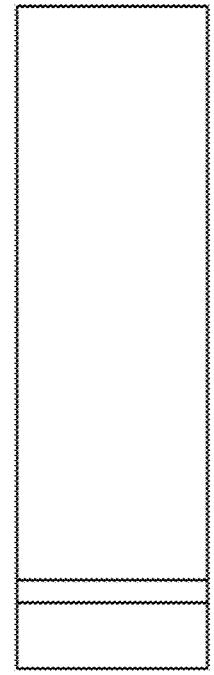
Figure 12A:
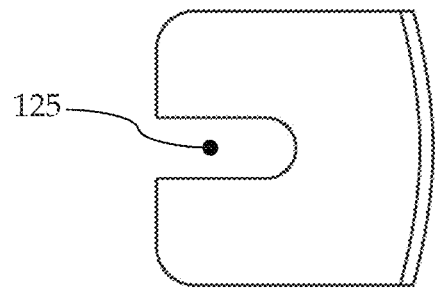
FIGS. 12A to 12C illustrate a syringe finger rest attach embodiment, without syringe.
Figure 12B:
Figure 12C:
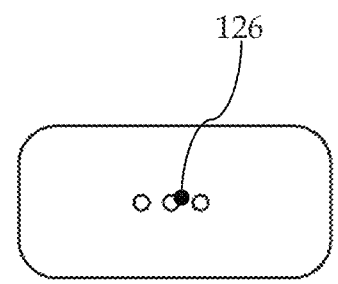
Figure 13A:
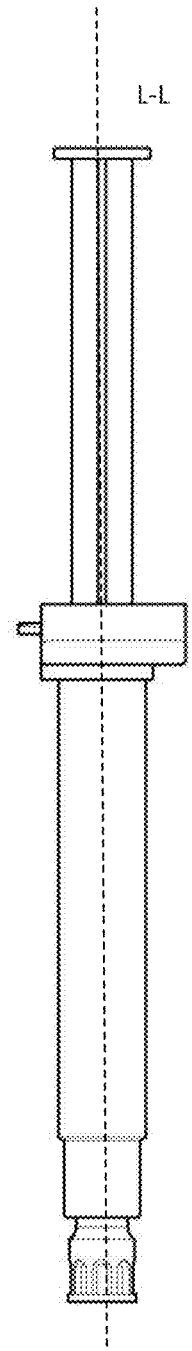
FIGS. 13A and 13B illustrate a syringe with and without syringe finger rest attach embodiment, with—side view.
Figure 13B:
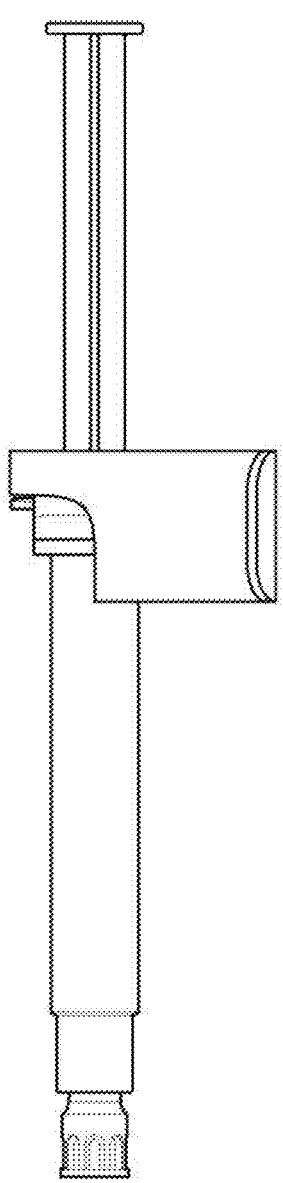
Figure 14A:
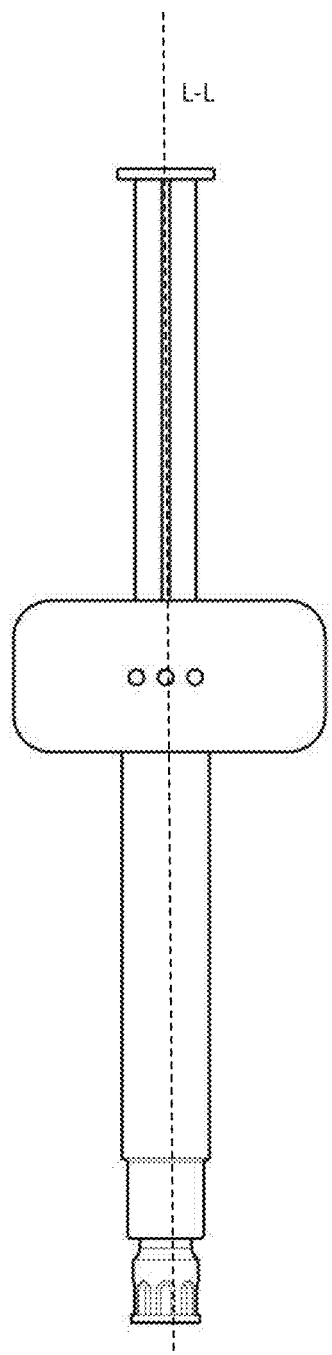
FIGS. 14A and 14B illustrate a syringe with and without syringe finger rest attach embodiment, with—front view.
Figure 14B:
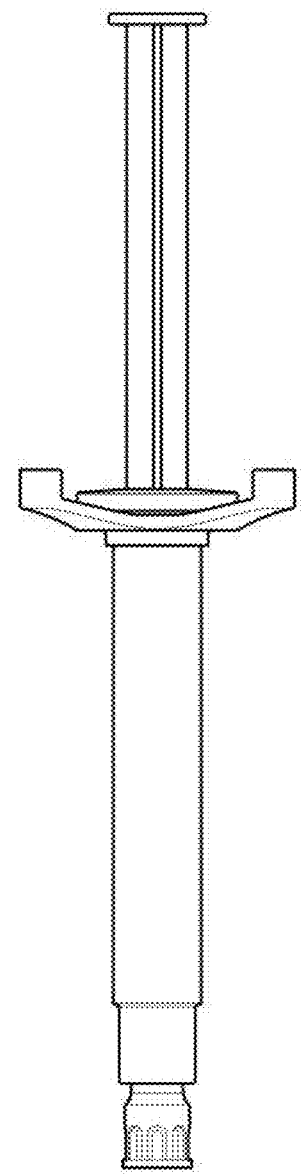
Figure 15A:
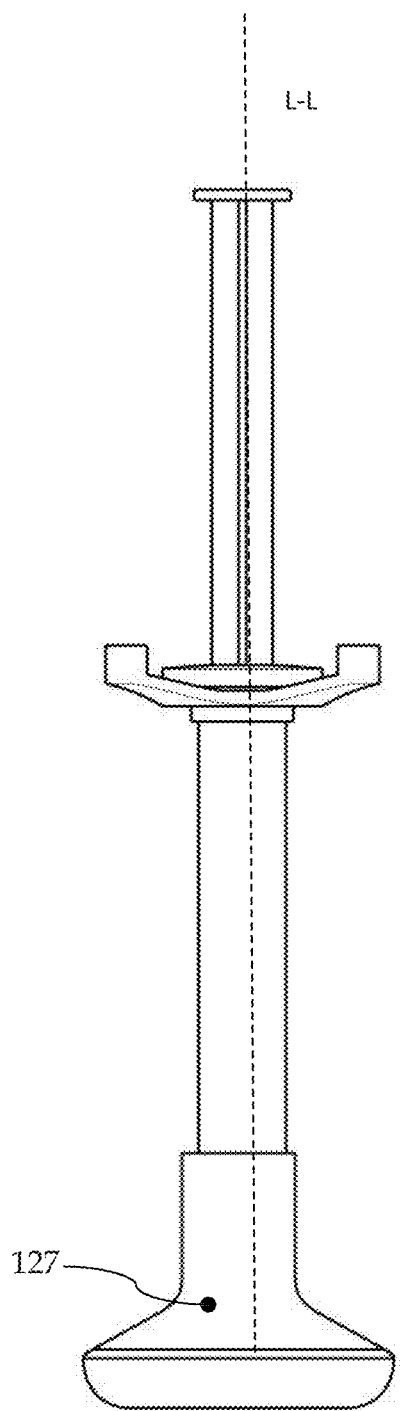
FIGS. 15A and 15B illustrate a syringe puck embodiment, with syringe.
Figure 15B:
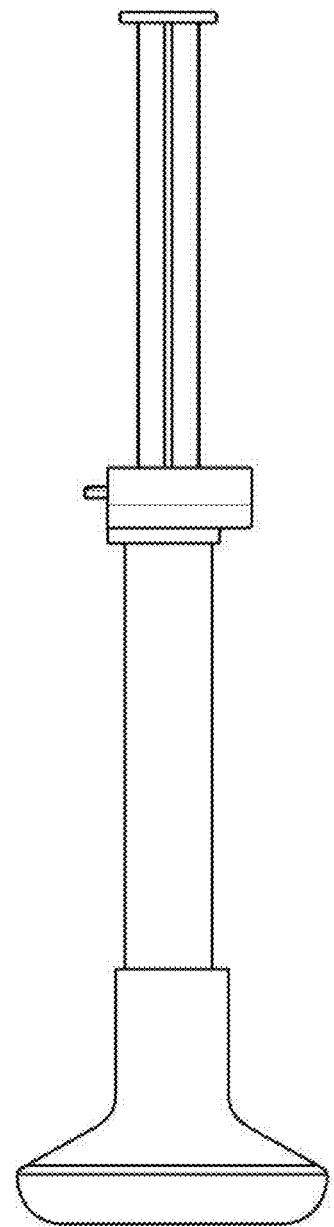
Figure 16A:
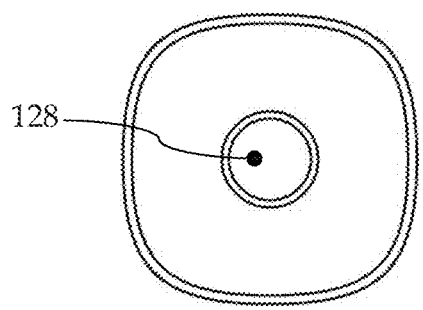
FIGS. 16A and 16B illustrate a syringe puck embodiment, without syringe
Figure 16B:
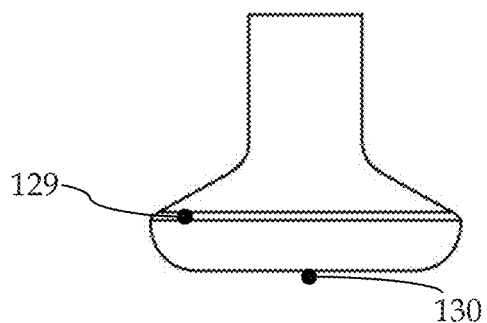

The embodiment shown in FIG. 6-FIG. 9C contains the syringe and provides feedback to the user while they are shaking the syringe. The device housing is opened by pressing on the lid catch 120; a syringe 117 is placed in the case liner 115 where it is retained by a spring clip 118 as shown in FIG. 7. Alternatively, the syringe could be retained by case lid 113 when the device housing is closed. Case lid 113 pivots around the case syringe 116 enclosing the syringe as shown in FIG. 8. The case includes flat surfaces on the case base 148 and case top 149 (FIGS. 9A to 9C), such that when placed on a desktop or work top it will not roll off. The case is closed and retained in a closed position by the lid catch 120. The outer shape of the case is designed to allow for users to hold it comfortably and securely when shaking. Shaking motion is measured using the internal electronic system, and the device state is communicated in two simultaneous ways. The first communication method is with light emitted from the light emitting panel 119, and amber light indicates that a shake cycle is in progress; and a green light indicates that it is completed. The second simultaneous feedback method is tactile. An intermittent vibration transmitted to the holding hand indicates that the shake cycle is in progress which changes to a continuous vibration when the shake cycle is completed. Furthermore the intermittent vibration emitted during the shake cycle is set at a frequency of approximately 3 Hz to reinforce the frequency and speed of shake required for optimum mixing, exploiting the tendency for humans to match repetitive behavior to percussive stimuli. The light emitting panel turning green indicates to the user to remove the syringe and continue with the drug administration process. This embodiment may be further developed with a syringe lock out feature. This feature would detect the presence of the syringe inside, lock the case in the closed state and only unlock the case when sufficient time and shake vigor have been achieved. In addition, if the user does not open the case to remove the syringe for injection within a specified time period, the case could re-lock itself, and/or the light could turn amber again, indicating that the device housing must be shaken again to re-suspend the particles before the syringe can be used.

Embodiment 4—Pot

The embodiment shown in FIGS. 10A to 11C includes an elongated body housing approximately the same length as the syringe barrel. The syringe is inserted into a syringe receiving hole 123 in the body housing and is retained by the compressive force applied by the fingers between the syringe finger flange 101 and the device body housing base 124. When the coupled device and syringe are shaken, motion is measured using the internal electronic system, and the device state is communicated in two simultaneous ways. The first communication method is with light emitted from the light emitting band 122, and amber light indicates that a shake cycle is in progress; and a green light indicates that it is completed. The second simultaneous feedback method is tactile. An intermittent vibration transmitted to the holding hand indicates that the shake cycle is in progress which changes to a continuous tone when the shake cycle is completed. Furthermore, the intermittent vibration emitted during the shake cycle is set at a frequency of approximately 3 Hz to reinforce the frequency and speed of shake required for optimum mixing, exploiting the tendency for humans to match repetitive behavior to percussive stimuli. The light emitting panel turning green indicates to the user to remove the syringe and continue with the drug administration process. As with other embodiments, further means of supplemental communication may be included, such as audible or tactile vibrating feedback, and a timing function can be used to signal the user if the syringe has not been removed from the device before a specified time period, indicating that the device must be shaken again to re-suspend the particles prior to performing the injection. A switch internal to receiving hold 123 would be used to detect when the syringe is attached to the device.

Embodiment 5—Finger Rest Attachment

The embodiment shown in FIGS. 12A to 12C, FIGS. 13A and 13B and FIGS. 14A and 14B is similar to embodiment 2, in that it attaches to the syringe. It is shown on the syringe in FIG. 13B and FIG. 14A. The syringe fits and is retained in the syringe accepting slot 125. The electronic system is housed within, and communicates to the user via the light panel 126 on the front face. An orange color indicates when the device is sensing and this turns green when it has been shaken sufficiently. As with other embodiments, further means of supplemental communication may be included, such as audible or tactile vibrating feedback.

Embodiment 6—Puck

The embodiment shown in FIGS. 15A and 15B and FIGS. 16A and 16B is similar to embodiment 4, in that it fits to the bottom of the syringe but is a much more compact design. It may include a body housing 127 with syringe accepting hole 128. The interface is provided by a circumferential light emitting band 129 around the diameter of the base of the form. In use, the syringe is inserted into the syringe accepting hole 128 and is held in place with the user's thumb on the underside thumb grip 130. As with other embodiments, further means of supplemental communication may be included, such as audible or tactile vibrating feedback.

Embodiment 7—Evoke

Figure 17A:
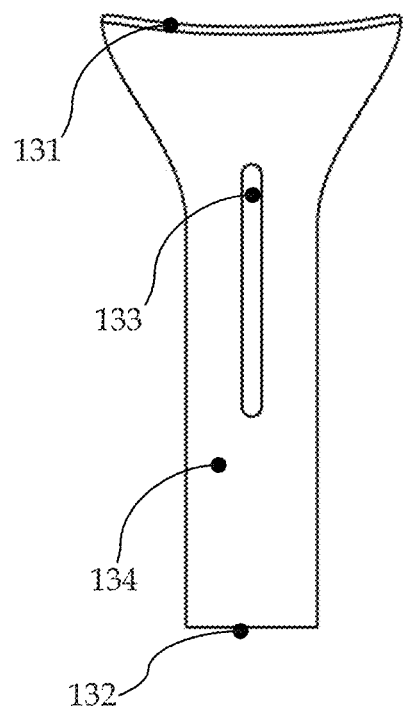
FIGS. 17A and 17B illustrate a trainer evoke embodiment.
Figure 17B:
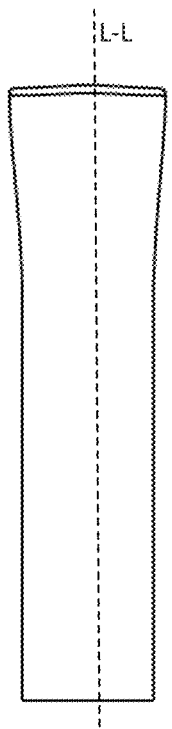
Figure 18:
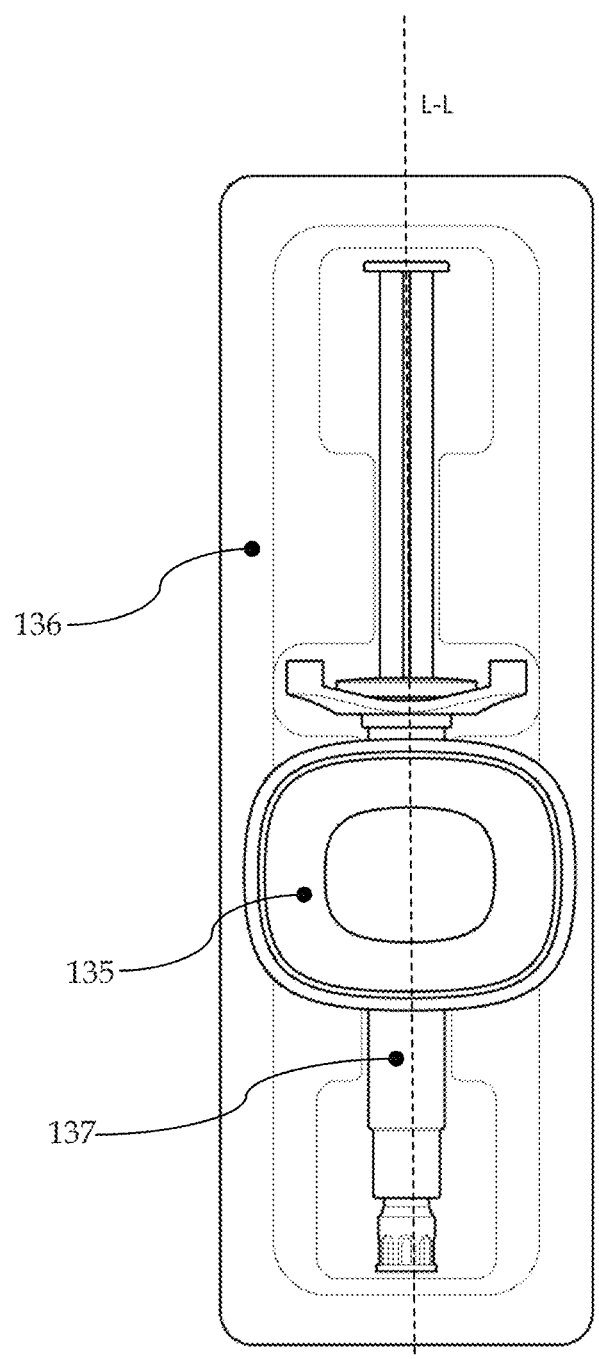
FIG. 18 illustrates a packaging attachment embodiment A, attached to syringe while in tray.
Figure 19A:
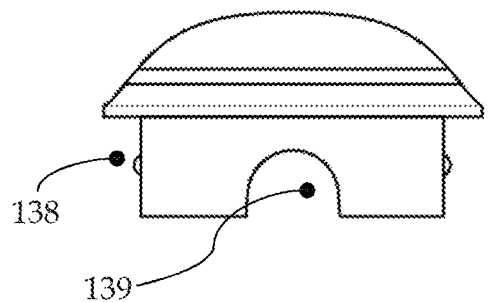
FIGS. 19A to 19C illustrate a packaging attachment embodiment A, detached from syringe.
Figure 19B:
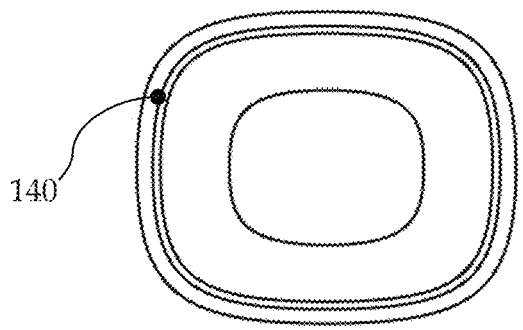
Figure 19C:
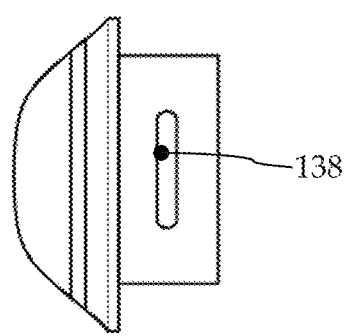

The embodiment shown in FIGS. 17A and 17B is similar to embodiment 1 of FIGS. 1B and 2A to 2D. It is a stand-alone device, which does not interact with the syringe, intended to be used in advance of the administration process. The user may practice shaking in advance of shaking the real syringe. It may include the device body housing 134, at either end of is the finger grip 131 and the thumb grip 132. The distance between finger grip and thumb grip is similar to the distance between the syringe finger grip and rubber stopper, to ensure it feels similar in the hand. When the user shakes the device, the device detects the forces applied and emits an amber light from the light emitting window 133. The light turns green when sufficiently vigorous shaking has occurred for sufficient time. As with other embodiments, further means of supplemental communication may be included, such as audible or tactile vibrating feedback.

Embodiment 8—Packaging B

Figure 20:
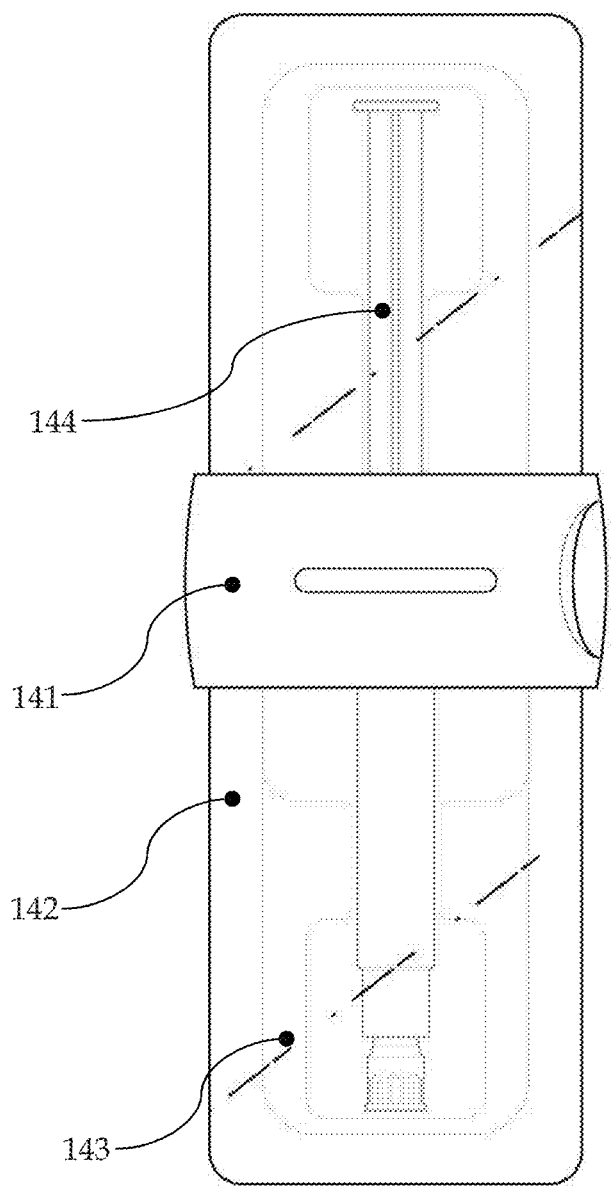
FIG. 20 illustrates a packaging attachment embodiment B, attached to syringe tray.
Figure 21A:
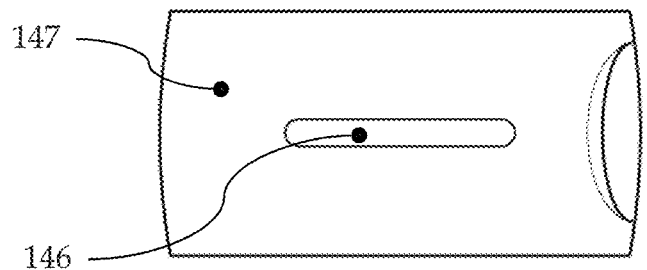
FIGS. 21A to 21C illustrate a packaging attachment embodiment B, detached from syringe tray.
Figure 21B:
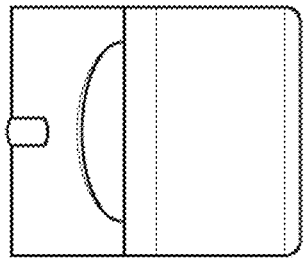
Figure 21C:
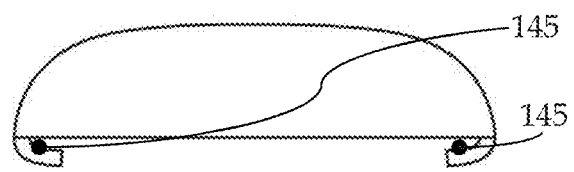

With reference to FIG. 20 and FISG. 21A to 21C, this embodiment is similar to embodiment 8, in that the device 141 attaches to the syringe blister packaging 142 while the syringe 144 is contained within. In this embodiment, the protective film 143 is still in place on top of the blister tray 142. With reference to FIGS. 21A to 21C the device is attached to the blister tray by sliding it along the length of the blister tray and is retained against the blister tray by means of return clips 145 on the underside of the device. The body housing of the device 147 includes means of communication, a light emitting strip 146. As with other embodiments the electronic system in the device detects the onset of shaking and starts to monitor the vigor and duration of shaking. While doing so, the light emitting strip 146 emits amber light. Once sufficient vigor and duration have been achieved the light changes to green. After shaking is completed the device is removed from the blister tray 142; the blister tray film 143 is peeled off and the device is used normally as per the syringe administration instructions. As with other embodiments, further means of supplemental communication may be included, such as audible or tactile vibrating feedback.

It is noted that during formulation development for Invega Sustenna Three Month, the required duration and vigor required were identified and quantified as 15 seconds of vigorous shaking. Vigorous shaking was initially defined using a training video in which an expert experienced in the correct preparation of the pharmaceutical product shakes a syringe for the required 15 seconds at the required level of vigor. Video analysis was used to estimate the amplitude and frequency of the demonstrated shake, finding that shake amplitude of approximately 40 cm was used at a frequency of 3.4 hertz. Assuming simple harmonic motion it was calculated that the syringe was experiencing a maximum acceleration of 9.3 g. This provides an indication of the required accelerations imparted on the fluid to achieve sufficient mixing as recommended by an expert in the preparation of such a formulation.

Figure 22:
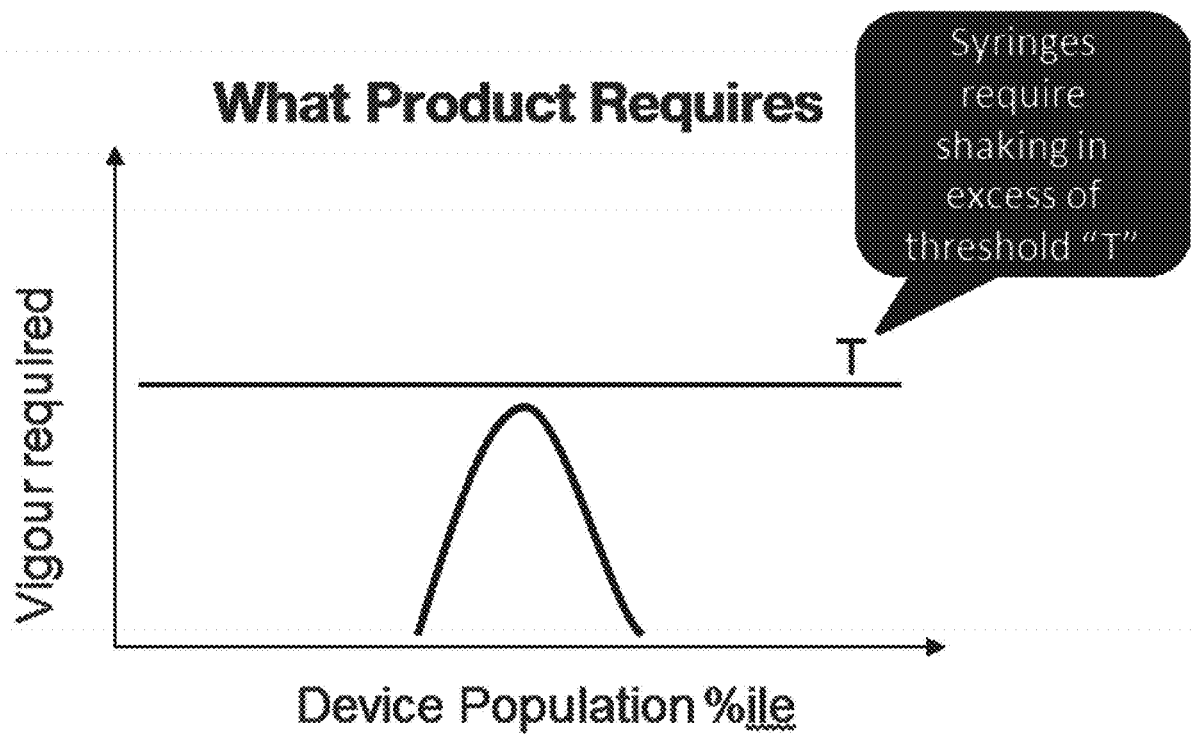
FIG. 22 is a chart illustrating the threshold requirement for a device containing sediment.

The failure mode associated with not mixing the syringe sufficiently is a failure to administer the full dose from the syringe. This occurs because insufficiently shaken syringes contain residual sediment which can block, or partially block, the syringe or needle during administration. Therefore syringes containing fluids with different sediment properties such as mass, density, and concentration can be quantified in terms of the required mixing vigor by applying controlled and known levels of acceleration (by experimental means) measuring the force required to eject the fluid from a syringe. Using such methods, different shake vigor thresholds may be determined for different fluid with different properties. FIG. 22 illustrates the device requirement for a threshold exceeding the intrinsic variability in the device population.

Figure 23:
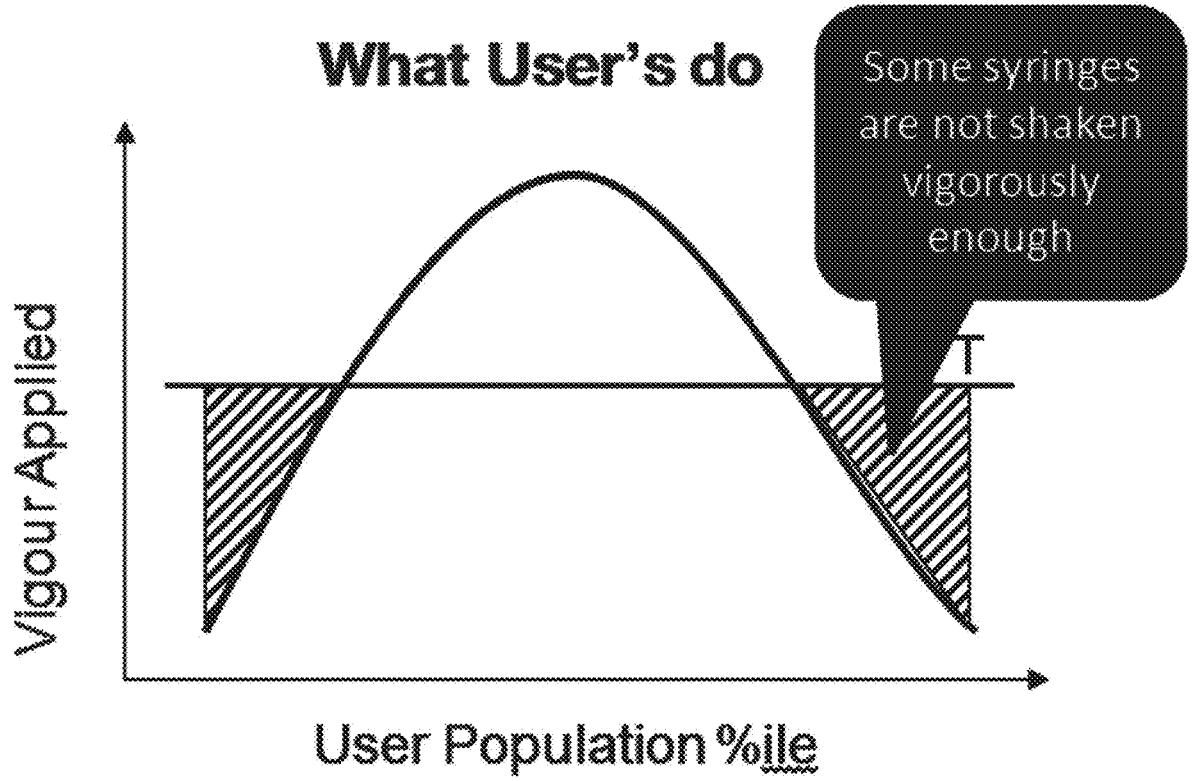
FIG. 23 is a chart illustrating how a proportion of users will fail to provide sufficient vigor to adequately mix the product un-aided.
Figure 24:
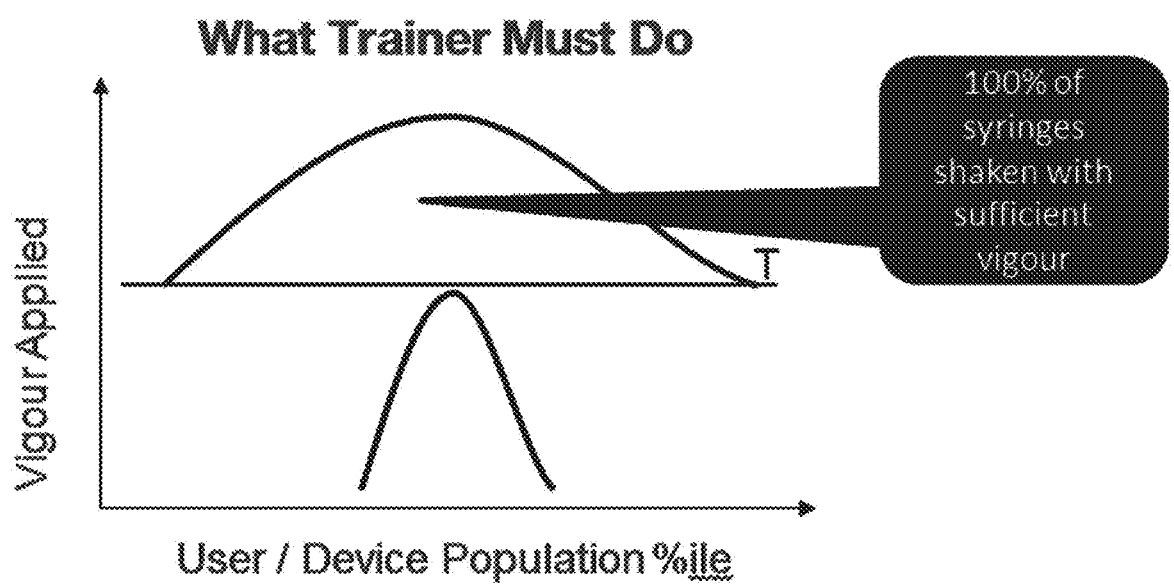
FIG. 24 is a chart illustrating the role of a device or aid, to modify user behavior so all shake with sufficient vigor to exceed the require threshold.

Once the required threshold is determined, the behavior of users should also be understood. Different users will have different capabilities, strengths, habits and expectations; therefore, there is in inherent variability in the way each interprets the instruction "shake vigorously" and some will naturally fail to meet the required threshold as illustrated in the chart in FIG. 23. Moreover, different users employ different shaking techniques, which some of which will be more vigorous than others. Acknowledging this variability, and that a minimum shake time and vigor are required leads to the conclusion that a need exists for the device described in this disclosure. The device can communicate the required time and vigor to the user, and modify behavior, increasing the likelihood of the user achieving the minimum required level of mixing. The subsequent effect of the device on the behavior across a population of users is illustrated in FIG. 24.

Once the threshold requirements and behavior modification goals are understood, consideration can be given to the various embodiments of form and function that might elicit the desired behavior modification. Such embodiments may either be used as a stand-alone device or as an in process device.

A stand-alone device is used in isolation of the administration process, providing the user an opportunity to shake a device and learn what level of vigor is required when they come to shake the real device. Such a stand-alone device may have a form factor close to that of the syringe so it may represent the experience of shaking the real syringe a closely as possible. Other form factors may also be used. For example, if the drug comes in a vial, a vial shaped device would be more appropriate.

Figure 25:
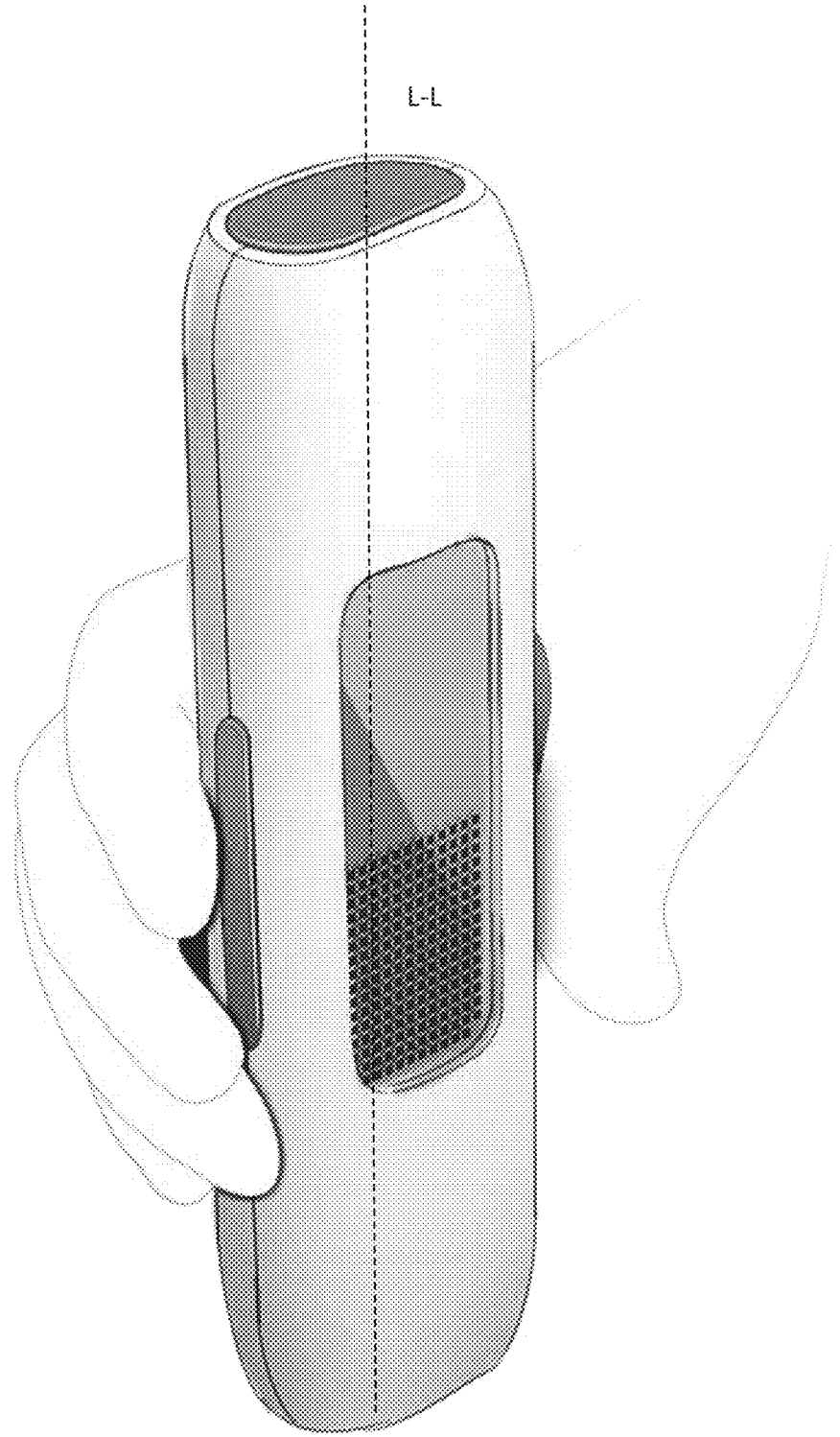
FIG. 25 illustrates a syringe case embodiment with LCD display—sedimentation mixing represented using display.

An assistive device is required to couple with, attach to, or encase the real syringe. As such means of coupling, attaching or encasing are required. This leads to varied opportunities for several form factors illustrated in FIGS. 1B-21C. Several means of communicating the device state to the user are possible. As previously described, they may include lights of different color or state (flashing or steady state); they may include audible means such as buzzers and speakers; and they may include tactile means such as vibrations. Further means are possible as shown in FIG. 25, such as a LCD (liquid Crystal Display) or similar, which may use graphical means to communicate the device state. An LCD may be used as a segment display to communicate device state through words and icons, or it may be used as a metaphorical indication of the mix state of the solution such as described in FIGS. 26A to 26D. In this case, LCD segments or pixels are switched on or off to create a visual indication of particles mixing with solution. On the left side of FIG. 26, darkly colored pixels in the lower portion of the display represent the presence of sediment in the bottom of the syringe. When shaking is detected by the electronic system, different pixels are switched on and off across the whole screen to indicate mixing is in progress, and when sufficient mixing is achieved the LCD can show a uniform homogenous color across the whole screen, indicating that the solution is also in a uniform homogeneous state.

By virtue of various embodiments of the invention, certain benefits were realized where the invention is configured as a stand-alone training device: (a) It makes the user aware of what the required shake time is; they learn through experience, (b) It allows the user to experience what the required level of shake vigor is, (c) It teaches the user what duration and level of vigor is required for the real device without impeding the normal administration process flow (d), It allows a device to have a form factor very close to that of the real syringe, (e), It allows the user to develop their skills so they are able to shake syringe sufficiently without having to rely on assistive aids, and (f) It is independent of the actual injection process and thus does not overly complicate it.

Other benefits were also realized when the invention is configured as an actual or "in-process" device: (a) It makes the user aware of what the required shake time is; they learn through experience, (b) It allows the user to experience what the required level of shake vigor is, (c) When attached to the syringe it allows the actual syringe to be shaken, providing the user with real time reassurance that it has been shaken adequately, and (d) If used correctly it reduces the chance of a real syringe being shaken insufficiently.

It is noted that these embodiments have been prototyped for testing with multiphase injectable pharmaceutical solutions. From such testing, a version has been selected for commercialization with a product with the trademark of INVEGA TRINZA™, which product is planned for distribution by Janssen Pharmaceuticals, Inc. Titusville, N.J. 08560. It is also noted that the proposed commercial version of the invention is intended to be utilized with INVEGA TRINZA™ in which a copy of the product label is attached to the appendix of this application, and such product label for INVEGA TRINZA™ is intended to be part of this patent application.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

In addition to the embodiments and disclosure provided above, which may be claimed individually, separately, in part or in combination, with features from the entire disclosure provided herein, the following numbered embodiments may be claimed individually, separately, in part or in combination, with features from the entire disclosure provided herein:

1. A device for training users in a proper mixing of pharmaceutical components or a device for aiding in the mixing and administration of pharmaceutical components, or a device for mixing and administering pharmaceutical components, the device comprising:
    a housing for receiving a pharmaceutical delivery device containing the pharmaceutical components;
    a microcontroller disposed in the housing; and
    a motion/orientation detection device disposed within or on the housing and in communication with the microcontroller.
2. The device of numbered embodiment 1, wherein the motion/orientation detection device is electrically connected to the microcontroller.
3. The device of any one of the preceding numbered embodiments, wherein the motion/orientation detection device comprises a device configured to detect one or both of: motion; and orientation of the housing with respect to the ground.
4. The device of any one of the preceding numbered embodiments, wherein the motion/orientation detection device is configured to detect a motion of the housing and provide a signal indicative of such motion to the microcontroller.
5. The device of any one of the preceding numbered embodiments, wherein the motion/orientation detection device is configured to detect an orientation of the housing and provide a signal indicative of such orientation to the microcontroller.
6. The device of any one of the preceding numbered embodiments, further comprising a user notification device.
7. The device of numbered embodiment 6, wherein the user notification device comprises one or more of: a display, a tactile feedback unit, a light emitting device and/or a vibratory alert unit.
8. The device of numbered embodiment 6 or numbered embodiment 7, wherein the user notification device is mounted on an external surface of the housing for notifying a user as to its status.
9. The device of any one of the preceding numbered embodiments when dependent on any one of numbered embodiments 6 to 8, wherein the microcontroller is configured to indicate via the user notification device as to whether the motion and/or orientation of the housing being shaken during one of a drug mixing and administration, or a training event, is sufficient enough for satisfactory mixing of the pharmaceutical components for delivery.
10. The device of numbered embodiment 9, wherein the user notification device is a display and the microcontroller is configured to indicate via the display the state of mixing of the pharmaceutical components in a real-time manner.
11. The device of numbered embodiment 10, wherein the microcontroller is configured to change progressively the color and or pattern of one or more display elements on the display as shaking takes place until sufficient shaking has taken place for satisfactory mixing of the pharmaceutical components for delivery.
12. The device of numbered embodiment 10, wherein the microcontroller is configured to display two types of display elements on the display which are grouped together in two discrete portions of the display prior to commencement of shaking, and which progressively mix which each other on the display so long as shaking continues at a sufficient enough or pre-defined force and/or for a sufficient enough or predefined duration, until such time that it is determined that sufficient shaking has taken place for satisfactory mixing of the pharmaceutical components for delivery, at which time the two types of display elements are wholly integrated with each other in a regular pattern across the display.
13. The device of any one of numbered embodiments 9 to 12, wherein the microcontroller is configured to determine whether there is satisfactory mixing with respect to one or more predetermined thresholds including magnitude of the force applied during shaking, the orientation of the housing and duration of such shaking.
14. The device of any one of the preceding numbered embodiments, wherein the movement/orientation detection device comprises an accelerometer.
15. The device of numbered embodiment 14, wherein the accelerometer comprises a 3-axis accelerometer.
16. The device of any one of the preceding numbered embodiments, further comprising a power source disposed in the housing.
17. The device of numbered embodiment 16, wherein the microcontroller is, when active, electrically powered by the power source.
18. The device of any one of the preceding numbered embodiments, further comprising a start switch electrically connected to the microcontroller.
19. The device of numbered embodiment 18, wherein the start switch is configured to activate the microcontroller from a power conservation mode into an active mode upon detection of movement of the housing during one of a drug mixing and administration event, or a training event.
20. The device of numbered embodiment 19, wherein the microcontroller is configured, during the power conservation mode, to draw reduced power with respect to the active mode, or no power at all, from the power source.
21. The device of any one of numbered embodiments 18 to 20, wherein the start switch is the motion/orientation detection device.

22. The device of any one of numbered embodiments 18 to 20, wherein the start switch is separate to the motion/orientation detection device.
23. The device of any one of the preceding numbered embodiments, wherein the microcontroller is configured to detect, during one of a drug mixing and administration or a training event, when shaking of the housing has ended prematurely for sufficient enough mixing of the components, or if the level of shaking vigor of the housing has reduced to a level below a pre-set threshold for sufficient enough mixing of the components, and, if so, to enter a pause mode to restart shaking.
24. The device of numbered embodiment 23, wherein the pause mode is notified to the user via the user notification device.
25. The device of any one of the preceding numbered embodiments, wherein the microcontroller is configured, during one of a drug mixing and administration or a training event, to set a timer and determine when a maximum allowable time has elapsed after sufficient shaking of the housing has completed, and is configured, if the maximum allowable time has elapsed to warn a user via the user notification device to shake the device again.
26. The device of any one of the preceding numbered embodiments, wherein the housing extends along a longitudinal axis of the device.
27. The device of any one of the preceding numbered embodiments, wherein the pharmaceutical delivery device comprises a syringe or vial.
28. The device of numbered embodiment 27, when dependent on numbered embodiment 26, wherein the housing comprises a syringe barrel element with finger flange and one end and a barrel tip spaced apart along the longitudinal axis.
29. The device of any one of numbered embodiments 27 or 28, wherein the housing comprises a body with a slot sized to accept a syringe barrel or a vial containing the pharmaceutical components.
30. The device of numbered embodiment 29, wherein the slot is aligned with the longitudinal axis of the housing, and the longitudinal axis of the syringe barrel or the vial.
31. The device of any one of numbered embodiments 27 to 30, wherein the housing is provided with a compartment and a lid to receive an entire syringe or vial.
32. The device of numbered embodiment 31, wherein the compartment is dimensioned to receive the entire syringe or vial snuggly and hold it securely within the housing.
33. The device of any one of numbered embodiments 27 to 32, wherein the housing comprises an elongated body approximately the same, or slightly greater than the length of a syringe barrel, such that a syringe is inserted into a syringe receiving hole in the body and retained by the compressive force applied by the finger-like members between a syringe finger flange and a body base.
34. The device of any one of numbered embodiments 27 to 33, wherein the housing comprises a body with a syringe accepting slot sized to accept a syringe barrel.
35. The device of any one of numbered embodiments 27 to 34, wherein the housing comprises a puck-like body with a syringe accepting hole so that, in use, a syringe is inserted into the syringe accepting hole and is held in place with a user's thumb on an underside thumb grip.
36. The device of any one of numbered embodiments 27 to 35, wherein the housing comprises an opening through which a discharge nozzle of the syringe or vial extends, or comprises an opening through which at least a portion of the syringe barrel adjacent the syringe's discharge nozzle can extend.
37. The device of any one of numbered embodiments 27 to 35, wherein the housing comprises a discharge nozzle which is adapted to be in fluid communication with the contents of a vial when such a vial is inserted into the housing.
38. The device of any one of numbered embodiments 27 to 35, wherein the syringe comprises a discharge member adapted upon application of force thereto to discharge the contents of the syringe.
39. The device of numbered embodiment 38, wherein the device further comprises an activator adapted to act upon the discharge member of the syringe, or act on the vial, to expel its contents through the discharge nozzle.
40. The device of numbered embodiment 38, wherein the housing further comprises an activator opening through which the discharge member of the syringe can extend for application of force directly by user from outside the housing.
41. The device of numbered embodiment 27, wherein the device is an attachment for a syringe and the housing is adapted to fit around a barrel of the syringe.
42. The device of numbered embodiment 41, wherein the housing is adapted to fit around only a portion of the barrel of the syringe.
43. The device of numbered embodiment 41 or 42, wherein the housing is formed of two hinged portions which rotate in a hinged manner with respect to each other, such that the hinged portions can close around the barrel and latch thereto.
44. The device of any one of the preceding numbered embodiments when dependent on any one of numbered embodiments 16 to 22, wherein the microcontroller is configured to detect low remaining power availability of the power source.
45. The device of numbered embodiment 44, wherein, when the microcontroller detects a low remaining power availability of the power source, it performs one or more of the following:
   issues an alert representative of the low remaining power availability to the user, for example via a user notification device; and
   prevents activation of the pharmaceutical delivery device for delivery of the pharmaceutical components to a user.
46. The device of any one of the preceding numbered embodiments, wherein the microcontroller is configured to detect an fault in the functioning of the device, for example in one or more of the motion/orientation detection device, the housing or its attachment to or containment of the pharmaceutical delivery device.
47. The device of numbered embodiment 46, wherein, when the microcontroller detects the error, it performs one or more of the following:
   issues an alert representative of the error to the user, for example via a user notification device; and
   prevents activation of the pharmaceutical delivery device for delivery of the pharmaceutical components to a user.

48. The device of any one of the preceding numbered embodiments, further comprising a delivery device identification unit in communication with the microcontroller.
49. The device of numbered embodiment 48, wherein the delivery device identification unit is configured to read data on data storage means of the delivery device characteristic of the pharmaceutical components contained therein and/or delivery device itself.
50. The device of numbered embodiment 49, wherein the data comprises one or more of:
    expiration date of the pharmaceutical components, whereby the microcontroller is configured to alert a user via a user notification device of the device if the current date as determined by the microcontroller exceeds the expiration date;
    data identifying the pharmaceutical components contained within the delivery device, for example data indicative of manufacturer or composition of the pharmaceutical components, whereby the microcontroller is configured to alert a user via a user notification device of the device if the data identifying the pharmaceutical components does not match or sufficiently correspond to permitted pharmaceutical components as stored in the microcontroller or in memory connected thereto;
    expiration date of the pharmaceutical components, whereby the microcontroller is configured to prevent activation of the pharmaceutical delivery device for delivery of the pharmaceutical components to a user if the current date as determined by the microcontroller exceeds the expiration date; and
    data identifying the pharmaceutical components contained within the delivery device, for example data indicative of manufacturer or composition of the pharmaceutical components, whereby the microcontroller is configured to prevent activation of the pharmaceutical delivery device for delivery of the pharmaceutical components to a user if the data identifying the pharmaceutical components does not match or sufficiently correspond to permitted pharmaceutical components as stored in the microcontroller or in memory connected thereto.
51. A method to direct a user on a proper drug mixing technique with the device of any one of claims 1 to 50, the method comprising at least the step of determining motion and/or orientation of the housing.
52. A device according to any one of claims 1 to 50, wherein one of the pharmaceutical components comprise an active pharmaceutical substance which is INVEGA TRINZA™ (see Appendix; section 11).
53. A device according to any one of claims 1 to 50, wherein one of the pharmaceutical components comprise an active pharmaceutical substance which comprises a racemic mixture of (+)- and (−)-paliperidone palmitate.
54. A device according to any one of claims 1 to 50, wherein one of the pharmaceutical components comprise an active pharmaceutical substance which is $C_{39}H_{57}FN_4O_4$.
55. The device of any one of claims 52 to 54, wherein the active pharmaceutical substance and/or device is for use in the treatment schizophrenia.
56. The device any one of claims 52 to 55, wherein at least one other of the pharmaceutical components comprises a fluid in which the active pharmaceutical substance is suspended.
57. A substance for use as one of the pharmaceutical components in the device of any one of claims 1 to 50, comprising an active pharmaceutical substance which is INVEGA TRINZA™ (see Appendix; section 11).
58. A substance for use as one of the pharmaceutical components in the device of any one of claims 1 to 50, comprising an active pharmaceutical substance which comprises a racemic mixture of (+)- and (−)-paliperidone palmitate.
59. A substance for use as one the pharmaceutical components in the device of any one of claims 1 to 50, comprising an active pharmaceutical substance which is $C_{39}H_{57}FN_4O_4$.
60. The substance of any one of claims 57 to 59 for use in the device for the treatment of schizophrenia.
100. Mimic trainer embodiment, plunger replacement
101. Finger flange
102. Light emitting feedback window
103. Barrel
104. Barrel tip
105. Syringe plunger rod
106. Syringe back stop
107. Syringe barrel
108. Rubber stopper
109. Barrel attach embodiment body
110. Light emitting feedback window
111. Syringe clamping slot
112. Syringe retaining spring clip
113. Case lid
114. Case body
115. Case liner
116. Case hinge
117. Syringe
118. Spring clip
119. Light emitting panel
120. Lid catch
121. Elongated body
122. Light emitting band
123. Syringe receiving hole
124. Base of body
125. Syringe accepting slot
126. Light panel
127. Body
128. Syringe accepting hole
129. Light emitting band
130. Thumb grip
131. Finger grip
132. Thumb grip
133. Light emitting window
134. Body
135. Body
136. Blister tray packaging
137. Syringe
138. Side interference clips
139. Syringe slot
140. Light emitting band
141. Device attached to blister tray
142. Blister tray
143. Blister tray film
144. Syringe
145. Return clips
146. Light emitting strip
147. Device Body
148. Case base
149. Case top
150. 3 Axis Accelerometer
151. Battery 152. Battery latch
153. Start switch
154. Microcontroller
155. User Notification

The invention claimed is:

1. A device for training users in a proper mixing of pharmaceutical components, the device comprising:
a housing that defines a longitudinal axis;
a power source disposed in the housing;
a microcontroller disposed in the housing and electrically powered by the power source;
a user notification device; and
an accelerometer disposed in the housing and electrically connected to the microcontroller so that the microcontroller is configured to detect a motion and orientation of the housing, commence a timer, and indicate via the user notification device as to whether the motion or orientation of the housing being shaken during one of a drug administration or a training event is sufficient with respect to predetermined thresholds including magnitude of the force applied during the shaking, the orientation of the housing, and duration of such shaking, and
wherein the microcontroller is configured to detect if the motion or orientation of the housing being shaken has reduced to a level below one or more of the predetermined thresholds, and if so to enter a pause mode of the timer to allow the user to restart the shaking during one of a drug administration or a training event, and
wherein the microcontroller is configured to reset the timer after a certain amount of time in the pause mode.

2. The device of claim 1, further comprising a start switch electrically connected to the microcontroller.

3. The device of claim 1, in which the accelerometer comprises a 3-axis accelerometer.

4. The device of claim 1, in which the accelerometer is configured to activate the microcontroller upon detection of movements of the housing during one of a drug administration or a training event.

5. The device of claim 1, in which the microcontroller is configured to detect when shaking of the housing has ended prematurely.

6. The device of claim 1, in which the microcontroller is configured to set a timer and determine when a maximum allowable time after shaking of the housing has elapsed to warn the user to shake the device again during one of a drug administration or a training event.

7. The device of claim 1, in which the housing comprises a syringe barrel having a finger flange at one end and a barrel tip at an opposite end, wherein the finger flange and barrel tip are spaced apart along the longitudinal axis.

8. The device of claim 1, in which the housing comprises a body with a slot sized to accept a syringe barrel or a vial.

9. The device of claim 1, in which the housing comprises a housing provided with a compartment and a lid to receive an entire syringe.

10. The device of claim 1, in which the housing comprises an elongated body approximately the same length as a syringe barrel such that a syringe is inserted into a syringe receiving hole in the body and retained by the compressive force applied by the finger-like members between a syringe finger flange and a body base.

11. The device of claim 1, in which the housing comprises a body with a syringe accepting slot sized to accept a syringe barrel.

12. The device of claim 1, in which the housing comprises a puck-like body having a recess adapted to receive a portion of a syringe.

13. A method to direct a user on a proper drug mixing technique with a training device or a device for mixing and assisting with the administration of the drug, that includes:
a housing that defines a longitudinal axis;
a power source disposed in the housing;
a microcontroller disposed in the housing and electrically powered by the power source;
a user notification device; and
an accelerometer disposed in the housing and electrically connected to the microcontroller to detect motion and orientation of such motion,
the method comprising the steps of:
determining from the accelerometer if the magnitude of the motion and orientation of the housing are sufficient with respect to predetermined thresholds including magnitude of the force applied during the shaking, the orientation of the housing, and duration of such shaking, and if so to commence a timer; and
announcing via the user notification device as to whether the motion or orientation of the housing being shaken during one of a drug administration or a training event meets the predetermined thresholds,
wherein the microcontroller is configured to detect if the motion or orientation of the housing being shaken has reduced to a level below one or more of the predetermined thresholds, and if so to enter a pause mode of the timer to allow the user to restart the shaking during one of a drug administration or a training event, and
wherein the microcontroller is configured to reset the timer after a certain amount of time in the pause mode.

14. The method of claim 13, wherein the device further includes a start switch electrically connected to the microcontroller.

15. The method of claim 13, in which the accelerometer comprises a 3-axis accelerometer.

16. The method of claim 13, in which the accelerometer is configured to activate the microcontroller upon detection of movements of the housing during one of a drug administration or a training event.

17. The method of claim 13, in which the microcontroller is configured to detect when shaking of the housing has ended prematurely.

18. The method of claim 13, in which the microcontroller is configured to set a timer and determine when a maximum allowable time after shaking of the housing has elapsed to warn the user to shake the device again during one of a drug administration or a training event.

19. The method of claim 13, in which the housing comprises a syringe barrel having a finger flange at one end and a barrel tip at an opposite end, wherein the finger flange and barrel tip are spaced apart along the longitudinal axis.

20. The method of claim 13, in which the housing comprises a body with a slot sized to accept a syringe barrel or a vial.

21. The method of claim 13, in which the housing comprises a housing provided with a compartment and a lid to receive an entire syringe.

22. The method of claim 13, in which the housing comprises an elongated body approximately the same length as a syringe barrel such that a syringe is inserted into a syringe receiving hole in the body and retained by the compressive force applied by the finger-like members between a syringe finger flange and a body base.

23. The method of claim 13, in which the housing comprises a body with a syringe accepting slot sized to accept a syringe barrel.

24. The method of claim 13, in which the housing comprises a puck-like body having a recess adapted to receive a portion of a syringe.

* * * * *

UNITED STATES PATENT AND TRADEMARK OFFICE
CERTIFICATE OF CORRECTION

| | |
|---|---|
| PATENT NO. | : 11,037,465 B2 |
| APPLICATION NO. | : 15/736328 |
| DATED | : June 15, 2021 |
| INVENTOR(S) | : Krulevitch et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 446 days.

Signed and Sealed this
Thirty-first Day of January, 2023

*Katherine Kelly Vidal*

Katherine Kelly Vidal
*Director of the United States Patent and Trademark Office*